US 9,183,351 B2

(12) United States Patent
Shusterman

(10) Patent No.: US 9,183,351 B2
(45) Date of Patent: Nov. 10, 2015

(54) MOBILE SYSTEM WITH NETWORK-DISTRIBUTED DATA PROCESSING FOR BIOMEDICAL APPLICATIONS

(71) Applicant: Vladimir Shusterman, Pittsburgh, PA (US)

(72) Inventor: Vladimir Shusterman, Pittsburgh, PA (US)

(*) Notice: Subject to any disclaimer, the term of this patent is extended or adjusted under 35 U.S.C. 154(b) by 0 days.

(21) Appl. No.: 13/784,815

(22) Filed: Mar. 4, 2013

(65) Prior Publication Data

US 2013/0231947 A1    Sep. 5, 2013

Related U.S. Application Data

(63) Continuation-in-part of application No. 12/885,520, filed on Sep. 19, 2010, now Pat. No. 8,388,530.

(51) Int. Cl.
| | | |
|---|---|---|
| *A61B 5/00* | (2006.01) | |
| *G06F 19/00* | (2011.01) | |
| *A61B 5/0205* | (2006.01) | |
| *A61B 5/0452* | (2006.01) | |
| *A61B 5/055* | (2006.01) | |
| *A61B 5/04* | (2006.01) | |
| *A61B 5/0428* | (2006.01) | |
| *A61B 6/03* | (2006.01) | |
| *A61B 6/00* | (2006.01) | |

(52) U.S. Cl.
CPC .......... *G06F 19/3418* (2013.01); *A61B 5/0022* (2013.01); *A61B 5/02055* (2013.01); *A61B 5/0452* (2013.01); *A61B 5/055* (2013.01); *A61B 5/7203* (2013.01); *G06F 19/345* (2013.01); *G06F 19/3443* (2013.01); *A61B 5/04004* (2013.01); *A61B 5/0428* (2013.01); *A61B 6/032* (2013.01); *A61B 6/5217* (2013.01)

(58) Field of Classification Search
CPC ...................................... A61B 5/0002–5/0022
USPC ........................................ 600/544, 508–523
See application file for complete search history.

(56) References Cited

U.S. PATENT DOCUMENTS

| | | | |
|---|---|---|---|
| 4,193,393 A | | 3/1980 | Schlager |
| 4,679,144 A | | 7/1987 | Cox et al. |
| 5,033,475 A | | 7/1991 | Ueda et al. |
| 5,463,548 A | | 10/1995 | Asada et al. |
| 5,501,229 A | | 3/1996 | Selker et al. |
| 5,544,044 A | | 8/1996 | Leatherman |
| 5,724,983 A | | 3/1998 | Selker et al. |
| 5,730,146 A | * | 3/1998 | Itil et al. ................. 600/545 |
| 5,791,342 A | * | 8/1998 | Woodard ................. 600/300 |
| 5,876,353 A | | 3/1999 | Riff |

(Continued)

OTHER PUBLICATIONS

V. Shusterman et al., Building and Application of Expert Systems for Differential Diagnostics of Cardiovascular Diseases, SAMS 1994, vol. 14, pp. 15-24.

(Continued)

*Primary Examiner* — Scott Getzow

(57) ABSTRACT

Adaptive system for medical monitoring distributes data processing among computing devices connected to a network to optimize usage of computational resources, network communication speed and user experience. Data processing is distributed into several levels with bi-directional communication between the levels (computing devices) to coordinate and adjust data compression, filtering, and analysis, as well as the size of buffered data available for transmission and/or receiving.

14 Claims, 11 Drawing Sheets

(56) References Cited

U.S. PATENT DOCUMENTS

| | | |
|---|---|---|
| 5,941,820 A | 8/1999 | Zimmerman |
| 5,956,013 A | 9/1999 | Raj et al. |
| 5,967,995 A | 10/1999 | Shusterman et al. |
| 6,038,439 A | 3/2000 | Rune |
| 6,057,758 A * | 5/2000 | Dempsey et al. ........ 340/539.12 |
| 6,108,635 A | 8/2000 | Herren et al. |
| 6,126,596 A | 10/2000 | Freedman |
| 6,154,668 A | 11/2000 | Pedersen et al. |
| 6,188,988 B1 | 2/2001 | Barry et al. |
| 6,221,011 B1 | 4/2001 | Bardy |
| 6,312,378 B1 | 11/2001 | Bardy |
| 6,336,903 B1 | 1/2002 | Bardy |
| 6,368,284 B1 | 4/2002 | Bardy |
| 6,440,066 B1 | 8/2002 | Bardy |
| 6,480,111 B2 | 11/2002 | Canady et al. |
| 6,681,131 B2 | 1/2004 | Kandori et al. |
| 6,807,438 B1 | 10/2004 | Brun Del Re et al. |
| 8,098,149 B2 | 1/2012 | Fisher et al. |
| 2004/0232912 A1 | 11/2004 | Tsukamoto et al. |
| 2005/0165323 A1 * | 7/2005 | Montgomery et al. ....... 600/544 |
| 2010/0049069 A1 | 2/2010 | Tarassenko et al. |
| 2010/0056939 A1 | 3/2010 | Tarassenko et al. |

OTHER PUBLICATIONS

Batchvarov et al., QT-RR Relationship in healthy subjects exhibits substantial intersubject variability and high intrasubject stability, Am J Physiol 282: H2356-H2363 2002.

Malik et al., Relation between QT and RR intervals is highly individual among healty subjects: implications for heart rate correction of the QT interval,Heart 2002 87 220-228.

Wu et al., Adaptive Noise Cancellation to Suppress Electrocardiography Artifacts During Real-Time Interventional MRI J.of Magnetic Resonance Imaging 33:1184-1193 2011.

* cited by examiner

MOBILE SYSTEM WITH NETWORK-DISTRIBUTED DATA PROCESSING FOR BIOMEDICAL APPLICATIONS

CROSS-REFERENCE TO RELATED APPLICATION

This is a continuation-in-part of application Ser. No. 12/885,520, filed Sep. 19, 2010, which was a continuation-in-part of application Ser. No. 11/641,268 filed Dec. 20, 2006, now U.S. Pat. No. 7,801,591, which was a continuation-in-part of application Ser. No. 10/816,638, filed Apr. 2, 2004, now U.S. Pat. No. 7,343,197, which was a continuation-in-part of application Ser. No. 10/124,651, filed Apr. 17, 2002, now U.S. Pat. No. 6,925,324, which was a continuation-in-part of application Ser. No. 09/583,668, filed May 30, 2000, now U.S. Pat. No. 6,389,308.

STATEMENT REGARDING FEDERALLY SPONSORED RESEARCH OR DEVELOPMENT

This invention was made with government support under the contract HHSN268201200066C awarded by the National Institutes of Health. The government has certain rights in the invention.

FIELD OF THE INVENTION

This invention relates to the field of biomedical devices and healthcare information management systems; and more specifically, to monitoring medical and health data (e.g., vital signs), diagnosis, analysis and decision support utilizing network (cloud) distributed data processing.

BACKGROUND OF THE INVENTION

Recent advancements in mobile computing (i.e., smart phone technologies) and physiological sensors have led to the development of miniaturized, wearable and easily attachable sensors, which can collect, process, and transmit data to a smart phone or other mobile devices and if necessary, send the data and/or alarms to healthcare professionals using wireless communication, specialized computer networks or the Internet. The mobile devices can also display the results of testing and send feedback (e.g., diagnosis and/or recommendations) from healthcare providers. Common examples of such systems include mobile (body-worn or attached) systems for monitoring vital signs, including heart rate, respiration, blood pressure, oxygen saturation, glucose and other physiological data, psychophysiological questionnaires and behavioral assessment programs. Such systems have been used by lay public (consumers) for personal health tracking and fitness training (e.g., exercise level, weight, diet, glucose level, etc.), as well as by healthcare providers for remote management of patients with chronic diseases (telemedicine). In the telemedicine applications, patients located at home are monitored by healthcare professionals remotely, from a hospital, clinic or monitoring facility. Some other examples of mobile systems include those utilized by emergency medical services (EMS) for monitoring and transmitting vital-sign data from the patient's home or ambulance to the healthcare professionals located at healthcare clinics, offices, hospitals or monitoring facilities.

Initially, mobile systems described above used computer networks and the Internet primarily for data transmission and storage. However, manual or semi-automatic processing and analyzing large amounts of continuously collected physiological data is time consuming and labor intensive, which creates a significant burden for the healthcare professionals (physicians, nurses, technicians) and leads to the information overload, errors and processing delays. Recently, such data-intensive problems, which are collectively referred to as the "big-data" problem, have been cited by the Office of Science and Technology as one of the most important challenges facing the Nation and its healthcare ("Big Data Research and Development Initiative"; Office of Science and Technology Policy, Mar. 29, 2012). This invention addresses several important types of Big Data; specifically, physiological, psychological, and behavioral data continuously or repeatedly collected over time, also referred to as the serial analysis or time-series analysis. One challenge of such analysis is related to the need to process large amounts of data collected over time (e.g., continuous electrocardiographic data, physical activity, blood pressure, blood glucose level, etc.) in the presence of various confounders, including changing environmental conditions, physical activity, psychological status, sleep/wake cycle, and so on. Another challenge is related to the necessity to combine information obtained from different sources (also referred to as the data fusion). For example, episodes of fainting (syncope) could be detected from the continuous tracking of physical activity and body position, whereas electrocardiogram and blood pressure can be useful for discerning underlying physiological mechanisms and triggers of fainting (e.g., sudden drop in blood pressure or cardiac arrhythmia). The analysis, however, is usually obscured by a number of confounders, including ambient noise, environmental factors, physiological and psychological activity. Combining (fusing) different types of information, such as physiological, behavioral, molecular, genomics and proteomics data, which have different time scales, resolutions and analysis rules, further increases the complexity of this problem.

Clearly, the solution of Big-Data problem lies in the utilization of network-distributed computing/processing (the Internet-cloud or cloud computing) and its resources. In particular, these resources can be used for processing vast amounts of continuously collected physiological data (electrocardiogram, blood pressure, glucose, etc.), as well as genetic, biochemical and molecular data. However, the development and implementation of such mobile, network-distributed systems are not trivial due to multiple requirements and constraints. In particular, 1) the data have to be processed accurately and quickly (either in real time or with minimal delays) on mobile systems with limited computational resources; 2) large amounts of data need to be transmitted to a network cloud or some other remote location over the network (e.g., healthcare institution) using wireless communication, which often has a limited or varying speed, connection quality and may experience delays or connection failures, and 3) the time-sensitive information (e.g., life-threatening abnormalities, vital signs, test responses) or trends (e.g., trends in blood pressure, physical activity, glucose level, cholesterol, weight, etc.) need to be presented in a short, clear and user-specific formats for healthcare professionals and individual consumers.

One commonly used approach is to perform data analysis at a single location (either at the user's location or on the cloud). For example, mobile devices can collect biomedical data (e.g., blood pressure, ECG, glucose level, weight, physical activity, body position, respiration, sleep duration/quality, behavioral and psychological status) and send it to a smart phone for processing and analysis (e.g., calculation of heart rate, calories, number of steps and other parameters). However, processing data locally, using a small processor with limited computational resources, while also performing several other concurrent functions (e.g., real-time data acquisition, formatting and display), usually requires simplified signal and/or image processing and may lead to inaccuracies in data analysis and/or display, as well processing time delays. Although this might be appropriate for some simple data types (e.g., number of steps or calories burned), many biomedical signals require advanced signal processing, pattern recognition and computational algorithms, which cannot be easily simplified. For example, accurate analysis of continuous electrocardiographic (ECG) signals usually requires filtering, advanced classification algorithms and pattern recognition methods. Although small microcontrollers with limited computational resources have been utilized for ECG processing in the implantable cardiac devices and ambulatory loop recorders, the results are usually substantially less accurate (misclassified cardiac beats and arrhythmias) compared to the analysis performed on a powerful computer utilizing advanced signal processing and pattern recognition algorithms.

Another commonly used approach is to collect the data on a mobile device (smart phone) or computer; send it to the Internet cloud (or network server) for analysis, and then forward the results to users' mobile devices or computers. This approach has become more common with the development of high-speed mobile communication. It is often implemented using JAVA programming environment, which makes the programs compatible with different types of mobile devices, computers and operating systems. In this approach, the user only has a simple viewer program, which receives and displays the data (e.g., ECG waveforms) and results of analysis performed on the cloud.

However, this approach also has drawbacks. One problem is related to the limited transmission speed and associated delays when large amounts of continuous, multichannel data are transmitted over a wide-area wireless network or the Internet. This problem becomes even more challenging when continuous data are transmitted from multiple users (e.g., multiple channels of continuous ECG, blood pressure, pulse oximetry and other data sampled at 1 kHz/channel), which can further increase time delays and network traffic overloads. When the data analysis is time sensitive, for example, when vital signs are analyzed by Emergency Medical Personnel in patients with chest pain, any time delay can be dangerous. To obviate this problem, U.S. Pat. No. 8,255,238 to Powell et. al. discloses a system for remote patient monitoring, which includes physiological sensor(s), a healthcare facility data processing/storage system and a remote handheld device. The system operates with the help of two graphical application program interface (API) systems. The $1^{st}$ API operates in conjunction with the healthcare facility data processing and storage system; it conditions (compresses) data for streaming across a cellular network and for reception and display on a handheld device. The $2^{nd}$ API operates in conjunction with the handheld device; it conditions (compresses) the data for faster display (rendering) on the handheld device.

SUMMARY OF THE INVENTION

This invention further extends the scope of methods and systems for multi-scale data processing and analysis described in Shusterman patents and pending application cross-referenced above. These methods and systems are particularly useful for computationally intensive tasks that can be distributed between devices and computers connected to a computer network, local-area network, wide-area network, wireless network or the Internet cloud.

Objectives and advantages of this invention include: 1) substantially continuous data compression, filtering and streaming from mobile data-collection devices to the cloud in near real time; 2) substantially continuous data compression, filtering and streaming data from the cloud to mobile devices for displaying in near real time; and 3) substantially continuous data compression, filtering and streaming from wireless data-collection modules to the receiving stations during magnetic-resonance imaging.

Briefly, the methods and systems for multi-scale data processing and analysis in Shusterman patents distribute data processing in scales (levels of detail, resolutions) according to computational resources, amount of data being processed, computational intensity of processing algorithms, the need to analyze and present the data in real time and/or on site, the need to transmit the data, results of analysis and/or alarms to a remote location, and other setting-specific and user-specific requirements. The $1^{st}$ scale (low-resolution) processing and analysis is preferably performed using mobile devices with limited computational resources (e.g., smart phone) by compressing (conditioning, rectifying) the signal and/or image data into a small set of primary elements (principal components, primary elements, leading indices), which represent the most important and/or typical features of the data in a succinct, compressed form onsite, in real time. For example, typical features of electrocardiographic signals may include duration of RR and QT-intervals, the amplitude of the ST-segment, and compressed patterns, segments or features of electrocardiographic waveforms (e.g., its basis vectors or eigenvectors and its respective coefficients). For pulse oximetry, these may include oxygen saturation and compressed features of the pulse-oximetry waveforms (e.g., its basis vectors or eigenvectors and its respective coefficients). For arterial blood pressure, these may include systolic and diastolic pressure and compressed features of the pressure waveforms (e.g., its basis vectors or eigenvectors and its respective coefficients). The $1^{st}$ scale processing is optimally suited for analyzing and presenting (displaying) most significant parameters or changes (e.g., changes of vital signs) on a handheld, mobile device (smart phone), personal computer or computer tablet. Information presentation is preferably user specific and may be presented in numeric, textual or graphical form; it may be color coded (e.g., green color representing normal values; yellow representing borderline and red representing abnormal values). Thus, the results of the $1^{st}$ scale of analysis serve two purposes: (i) they provide immediate, access to critical information (e.g., vital signs) locally, on-site; and (ii) allow fast and efficient data compression because transmitting small number of key indices (such as heart rate, blood pressure, amplitude of the electrocardiographic ST-segment) over a network (e.g., using a mobile, wireless cell phone, Wi-Fi, Bluetooth or other types of communication) is faster and more efficient than continuous transmission of raw signals. The raw signals can be stored locally, uploaded to the cloud or transmitted to a remote location, if needed.

The higher-scale (resolution) processing entails more advanced and computationally demanding (intensive) analysis, which requires greater computational resources and therefore is preferably performed on a powerful computer, network of computers such as the Internet cloud. This higher-scale processing is suitable for large amounts of long-term, continuous data or serially (repeatedly) collected short-term data (e.g., long-term recordings of vital signs or serially collected short-term measurements of vital signs, physical activity, psychological activity or behavioral status). In addition to the large data volumes, serial analysis is computationally demanding because of various confounding factors (e.g., ambient environmental noise, electromagnetic interference, movement artifacts, changes in sensor and/or body position, physiological activities, sleep, exercise and other factors). Processing accuracy and efficiency is optimized by determining an individual's serial reference (baseline) pattern and comparing newly collected data with an individual's baseline. I have shown that such analysis is particularly useful for detecting, clarifying, filtering, compressing and rectifying hidden structures or subtle changes and/or trends in serial data, which might otherwise escape detection by visual inspection or traditional statistical methods. In particular, I have shown that such a "personalized", multi-scale approach accurately tracks changes in an individual's data, including subtle, complex or gradual changes, including early warning signs of life-threatening clinical events.

In addition to the waveform patterns and their main characteristics (e.g., compressed waveforms, their segments, eigenvectors and respective coefficients), the results of the higher-scale processing may include patterns of changes or trends in the waveforms' patterns and typical features. The compression and analysis are performed on the time series of waveforms' patterns and their typical features (e.g., time series of beat-to-beat changes in heart rate, blood pressure or glucose level) to determine higher-order patterns of changes or trends in data, which may include subtle or complex serial changes in the electrocardiographic ST-segment due to ischemia or proarrhythmic lengthening of the electrocardiographic QT-intervals.

In addition, the higher-resolution analysis is useful for combining (fusing) serial data with other sources of information. Such data fusion may include several continuous signals, for example: 1) electrocardiogram, physical activity and body position to analyze the impact of the latter 2 factors on the ECG; 2) blood pressure and physical activity to assess the impact of physical activity on the dynamics of blood pressure and to detect syncope (episodes of fainting and falling); 3) respiration, body position and physical activity to examine the impact of physical activity on respiration, determine the presence of sleep apnea during nighttime. The data fusion is analogous to multidimensional scaling or combining different signals into a single, multidimensional space. Alternatively, the data fusion can be performed to combine data from continuous signals (e.g., blood pressure) and discrete information (e.g. psychological or behavioral assessment) to examine the impact of behavioral factors on blood pressure dynamics.

Thus, the $2^{nd}$ and/or higher scales of analysis are preferably performed either on a computer network or on the Internet cloud, using raw data and/or its key indicators (which represent the data in a compressed, conditioned and/or rectified form) obtained from the $1^{st}$ scale of analysis. These data can be transmitted from users' mobile phones or computers automatically or entered manually; examples of data that can be entered manually include body temperature, blood pressure and blood glucose level. The results of the $2^{nd}$ level of analysis are used in two ways: (i) compressed and conditioned (filtered) waveforms, their main characteristics (basis vectors and respective coefficients), as well as the most important quantitative indicators of significant changes and/or abnormalities are transmitted (or made available for viewing) to the healthcare providers and/or individual consumers. This textual messages, graphical and numerical feedback transmitted back to the smart phones, personal computers or other devices used by individual consumers and/or medical professionals; and (ii) they are transmitted back to the users' mobile or personal-computing devices for adapting ("personalizing") the thresholds, time windows and other parameters used for the $1^{st}$ level of analysis on mobile devices, smart phones or personal computers. Alternatively, this information can be made available for viewing and/or downloading from the cloud to a mobile phone and/or personal computers of an individual consumer (patient) and/or healthcare provider; however, the transmission is not performed automatically, but initiated per user's command.

An important feature of multi-scale analysis is an exchange of information between the processing scales, which are preferably distributed between personal/mobile devices and a computer network such as the Internet cloud. The $1^{st}$-level processing unit (e.g., smart phone) sends the data and the description of the set of primary elements, comprised of characteristic features, parameters and patterns, to the higher-level ($2^{nd}$-level) processing unit (cloud). The $2^{nd}$-level processing unit (cloud) receives both the data and the description/characteristic features of the $1^{st}$-level processing set used by each mobile unit. The $2^{nd}$-level, advanced processing determine characteristic (typical) features of data pattern in more detail and with greater accuracy, including an expanded set of analytical parameters, which represent both static and dynamical features of the signal in compressed form, as well as an individual's baseline pattern of short-term and long-term dynamics. This information or some of its elements in a compressed and/or rectified form (according to the description of the $1^{st}$-level set transmitted by the mobile device) are then transmitted back to the mobile device for adjusting (tailoring, fine-tuning) the $1^{st}$ level analysis. Such feedback information may include adjusted monitoring thresholds and/or alarms (e.g., dangerous or clinically significant levels of blood pressure, heart rate, tachycardia, bradycardia, pauses, atrial fibrillation, electrocardiographic ST and/or QT-interval, respiration, glucose, physical activity, syncope). If necessary, information from the $2^{nd}$-level analysis is also transmitted to a remote user (healthcare professional) and displayed in graphical, textual and/or numerical form on that user's mobile or computer device. The $2^{nd}$-level analysis performs an efficient compression, conditioning, and filtering of the data patterns, it minimizes the amount of information that needs to be transmitted to the $1^{st}$-level unit, as well as transmission times. In particular, the $2^{nd}$-level analysis can transmit a minimal number of eigenvectors and coefficients of an orthogonal linear decomposition, which provide the most accurate and parsimonious representation of waveform patterns (i.e., optimal compression). Other mathematical decompositions that are described in Shusterman patents and the patent application incorporated herein by reference can be used for this purpose as well.

The transmission and viewing is preferably performed asynchronously, allowing some amount of data being transmitted and stored in a local buffer, memory and/or other storage media of the mobile device before the user starts displaying and reviewing both the data stored in the buffer and received from the cloud in real time.

Applications of the present invention include but are not limited to the following examples: mobile, body-worn (or attached) systems for monitoring vital signs (electrocardiogram, heart rate, pulse oximetry, blood pressure, respiration, temperature, physical activity) and other physiological data, performing tests (stress test or tilt-table test), assessment of the psychophysiology and behavior using smart phone for remote communication, cloud-based analysis of large datasets (e.g., personalized genomics and/or proteomics data), as well as other applications useful for individual consumers (for personal monitoring of health and fitness) as well as for remote management of patients with chronic diseases performed by healthcare providers and telemedicine. This also includes mobile systems for transmitting medical (electrocardiographic, pulse oximetry, blood pressure and/or other vital signs) data by emergency medical services (EMS) to healthcare professionals located at healthcare clinics, offices, hospitals or centers.

Specific scenarios for distributing different levels of processing between mobile devices and a computer network or the cloud depend on the computational resources and speed of transmission lines. Examples of such distributed processing include:

1. The $1^{st}$ processing scale performed on a personal device (mobile device, smart phone, tablet computer, personal computer); whereas higher-scale processing is performed on the Internet cloud or network server.
2. The cloud receives data from personal devices and performs both 1st and higher-scale processing. Subsequently, the results and/or compressed waveforms are transmitted back to the personal device(s) to allow displaying and/or continuous streaming of data on personal/mobile devices, provide feedback messages, graphical summaries and numerical results to the individual user and/or healthcare professionals.
3. The cloud receives data from personal devices and performs both 1st and higher-scale processing. Subsequently, the results and/or compressed waveforms are transmitted back to the personal/mobile device(s), where the 1-st level processing is performed and/or adjusted to allow displaying and/or continuous streaming of data on personal devices, provide feedback messages, graphical summaries and numerical results to the individual user and/or healthcare professionals.
4. An adaptive combination of the two approaches described above is implemented according to the time constraints, data availability, and other setting and/or user-specific constraints.
5. The distribution of the $1^{st}$ and higher scales of analysis is dynamically adaptable for the availability, speed, quality and cost of the computational resources and transmission lines used for communication between the levels of analysis, as well as time sensitivity (urgency) of data analysis, distance between the location of patients and healthcare institution, patients' medical history, complaints, medications, changes in the patients' health and/or disease status, diagnosis, complications, presence and/or absence of healthcare professionals and other factors. For example, the system can dynamically re-allocate both the $1^{st}$ and $2^{nd}$ levels of processing to the local device or local-area network when more powerful computational resources become available. Alternatively, both the $1^{st}$ and $2^{nd}$ levels of processing can be shifted to the cloud if fast transmission lines become available, and/or the data need to be reviewed by healthcare professionals located at a remote location. Changes in patients condition that may require adjustments in allocation of the $1^{st}$ and/or higher processing scales include heart failure decompensation, high glucose level, high blood pressure, syncope, suspected myocardial infarction, arrhythmia, stroke and other emergencies, which may require shifting the $1^{st}$ level of processing and immediate display on the attending physician's mobile phone. Alternatively, both patient's and physician's mobile devices can be synchronized to perform the same level of processing, to allow the patient participation in healthcare management. This feature is particularly useful for managing chronic patients remotely.

The multi-scale processing and communication can be implemented either in Microsoft Visual Studio/.Net development environment, Java or Linux. The scale-1 processing module can be installed on a mobile device/smart phone, whereas higher scale processing can be implemented on the cloud with asynchronous communication between them via cell-phone line, Wi-Fi, wide-area network, DSL, cable (e.g., T1 cable) or other wireless communication links. In particular, the $1^{st}$-scale processing and display can be implemented using JAVA, JAVA script or Microsoft .net environment on a mobile phone. The higher-scale processing and serial analysis can be implemented in JAVA or Microsoft .net environment on the cloud. A user of a mobile device can have a limited-functionality program written, for example, in JAVA script and containing the scale-1 processing and display of compressed waveforms (electrocardiogram, blood pressure, respiration and other vital signs) and parameters (heart rate, glucose, respiration rate). This limited-functionality program will receive pre-processed (conditioned or compressed) waveforms and parameters from the higher-level processing module on the server implemented, for example, in JAVA or C#/C++(.net software development environment).

This invention also applies to and extends implementations of data buffering for continuous data streaming, processing and display. Real-time, circular buffering is a commonly used feature in many applications featuring continuous data acquisition, processing and display to avoid time delays. However, this patent application provides the know-how for efficient data compression and adaptive exchange between two buffered data streams, on a mobile device and on a cloud. The software on a cloud performs higher-scale processing and adaptive compression of data according to the computational resources on the mobile device and/or smart phone with scale-1 processing. The data buffering on a mobile device (smart phone) is constrained by its limited computational resources (memory and processor speed) and limited speed of wireless data speed/transfer rate. The Scale-2 processing performed on a cloud provides accurate and efficient means for data compression, rectification and filtering using adaptive processing and accurate identification of an individual's reference (baseline). Specific mathematical methods used for these purposes include but are not limited to orthogonal decompositions, methods of statistical analysis, signal processing, pattern recognition, time-series analysis and artificial intelligence, which are applied for compressing, conditioning and filtering serial health data, including physiological signals. The scale-2 processed and compressed data is sent from the cloud to the scale-1 buffer on a mobile device to allow faster and more efficient buffering, data streaming and display on the screen of a mobile device (smart phone). This patent application extends previously used methods for implementing efficient buffering by providing an adaptive, network distributed buffer (or a set of network-distributed buffers), in which the cloud pre-conditions (compresses/filters) the signals and sends them to the smart phone for real-time buffering and display. In addition, the cloud also may transmit to the smart phone's buffer (utilizing Scale-1 analysis) a set of primary elements derived from the statistics of the signals for displaying them on the phone's screen. The size of the data buffer can be adjusted according to the user's preferences or automatically adapted to the user's speed of data viewing or to the type of data and/or its processing and analysis.

This invention can be used for remote patient management as well as for general consumers' health and fitness applications. This invention can also be used for emergency medicine, to provide fast and efficient data transmission from the point-of-care or patient's home to physicians in the hospital and allowing physicians to display and process and analyze the data on their smart phones, other mobile devices, tablet computers, and personal computers. This invention also allows physicians and other medical personnel to download, display and quickly review data on their mobile devices at anytime, anywhere; while the data is being collected and transmitted in real time from patients at hospitals, point-of-care, on the road or at home.

Shusterman U.S. Pat. Nos. 7,801,591, 7,485,095, 7,343,197, 6,925,324, and 6,389,308 and pending patent application Ser. No. 12/885,520, filed Sep. 19, 2010 have shown that multi-scale, personalized (individually "tailored") analysis provides superior accuracy compared to population-derived estimates. The disclosures contained in those Shusterman patents and application are, by reference, incorporated herein in their entireties.

Among traditional statistical methods that are commonly used for the analysis of serial changes are paired tests and repeated-measures Analysis of Variance (ANOVA). Neither method, however, can account for complex individual patterns of serial dynamics. Analysis of such complex serial changes requires specialized statistical time-series or signal processing methods, which have been disclosed by Shusterman in U.S. Pat. Nos. 7,801,591, 7,485,095, 7,343,197, 6,925,324, and 6,389,308 and application Ser. No. 12/885,520. These methods may include mathematical decomposition, time-series analysis, mathematical modeling, computer modeling, signal processing, statistical analysis, and methods of artificial intelligence. Some examples of specific methods include hidden Markov models, orthogonal decomposition, non-orthogonal decomposition (independent component analysis), multidimensional scaling based on non-metric distances and mapping techniques, non-orthogonal linear mappings, nonlinear mappings and other methods, that make use of projection, re-scaling (change of variables), methods from the theories of singularities, bifurcations, catastrophes, and dynamical systems, and other statistical estimators, linear and nonlinear correlation, analysis of variance, cluster analysis, factor analysis, canonical analysis, regression and discriminant function analyses, and probabilistic methods, Bayesian probability and Mahalanobis distance, pattern recognition, fuzzy logic, neural networks, expert systems, and hybrid artificial intelligence systems.

This invention provides a method and system that can be used for at least one of information management, decision support, and diagnosis. The method and system distribute (structure) the information into at least two levels of detail (scales or resolutions). A low-resolution scale represents a snapshot measurement of at least one indicator (vital sign or primary element) such as heart rate or blood pressure. A higher resolution scale is designed to determine serial changes in each of the said primary elements. Low, intermediate and high-resolution scales can exchange information between each other for improving the analyses; the scales can be distributed vertically among the units connected by a network and defined according to the corresponding software and hardware resources. Uncertainty or probability of a diagnosis is tracked dynamically (the probabilities are updated periodically or quasi-periodically over time taking into account information available at each time point; new information is included in the analysis as it becomes available) based on the information availability or completeness relative to the total complete information at each level and at multiple levels. This structuring provides several advantages. First, it improves and optimizes the flow of information along the network. This feature is significant, since the volume of information provided by a multitude of diagnostic tests is high (such as electrocardiographic monitoring, magnetic resonance imaging (MRI), computed tomography (CT), CAT-scans, echocardiography, biochemical, and other tests) and increases with time. The structuring permits control of this high volume of information, so the most important information (vital signs) is analyzed on-line and on-site (Low-resolution), whereas the rest of the information, which includes subtle changes in patient's state, are detected and quantified using comparative analysis of serial data (Higher level of resolution). Such distribution of the enormous amount of medical information prevents information overload and ensures that the information is processed accurately and in a timely fashion, and allow medical professionals to receive adequate and accurate information about the patient tailored to the specific setting of the medical care and patient's profile.

Second, this multi-level structure also ensures adaptability of the system, in which the system processes all available data to learn the individual patient's pattern of normal range and abnormal variations. The adaptability is achieved by collecting and processing serial data at the higher scales and then, using this information at the lower scale to individually tailor (edit, adjust) the diagnostic and processing criteria (thresholds). Third, for reasons described above, this multi-level structure also optimizes bi-directional communication and personalized and timely advice and treatment of each patient.

Thus, by vertically distributing the analyses and representation in several levels, the system optimizes information flow, usage of medical knowledge, and improves accuracy of analysis of serial changes, and adaptability to each individual's data. Low, intermediate and high-resolution scales can exchange information between each other for improving the analyses; the scales can be distributed among the units connected by a network and defined according to the corresponding software and hardware resources. In addition, the system can be adapted to optimize usage of medical knowledge contained in medical journals, books, the Internet, and other materials for personalized analysis of serial data. The system optimizes and improves the information flow by vertically distributing it into several levels or Scales according to the importance and relevance of the information, and according to the available software and hardware resources. The low-resolution Scale I represents one-time, periodic, or quasi-periodic snapshot measurements of health data, such as heart rate, blood pressure, blood count, cardiac output, physical activity, temperature, and weight, referred to as the primary elements. The higher-resolution Scale II is used to analyze serial changes in each of these primary elements. Optionally, the $3^{rd}$ scale can be used to analyze combined serial changes of these primary elements. By using this personalized analysis, the system improves accuracy and clarity of analysis and representation of personalized serial analysis. These scales can also include medical knowledge from medical textbooks, journals, and other materials available on the computer network to improve personalized analysis.

Examples of such a multi-scale structure for analysis, representation, distribution and management of health data is presented in FIG. 1. As depicted in the figure, in the first (bottom) scale, data is collected from at least one, and preferably, a multitude of diagnostic devices, such as electrocardiographic, electroencephalographic, echocardiographic, magnetocardiographic, magnetic resonance imaging, computer tomography, thermometer, blood pressure tonometer, pulse oxymeter, impedance meter, genetic/DNA/genotype/proteomics/metabolomics measurements, MRI, CT, ultrasound, fluoroscopic, X-ray image, stress-test, physical activity test, neurographic recordings, biochemical tests, blood tests, enzyme tests, clinical symptoms, such as chest pain, shortness of breath, nausea, etc. These data can be collected as a one-time test, periodic, quasi-periodic, or continuous monitoring (measurements). At the low-resolution level (scale) I, these data are processed to extract the most important indicators (vital signs, diagnostic indicators) or primary elements, such as heart rate, blood pressure, magnitudes and durations of electrocardiographic waves (QRS, T, and P-waves, and ST-segment, T-wave alternans), cardiac output, respiration, temperature, neural activity, etc.

At the next level (scale) II, dynamics of each primary element (vital sign or diagnostic indicator) is analyzed using serial recordings obtained from the individual. The dynamical (serial) analysis is performed using the mathematical, modeling, probabilistic, pattern-recognition, time-series, signal-processing, statistical, computer, and artificial intelligence methods described below. In the simplest-case scenario, serial changes are analyzed using simple statistical parameters, such as the mean or median value, or the standard deviation (a square root of variance), or a range of variations (for example, 25%-75% range) of the time series of serial changes over a certain time interval. The serial changes in any of these statistical parameters or in the combination of these parameters can be estimated, for example, using a statistical test that determines the statistical significance of serial changes over time (for example, a non-parametric, Friedman ANOVA for repeated measurements or a paired t-test, or an ANOVA for repeated measurements), or using pre-selected or adaptive thresholds (for example, a threshold of 3 standard deviations can be used to detect significant changes in the mean values). As a result of this dynamic analysis, trends of changes are represented either as quantitative data, qualitative information, an advice, or graphs of trends in genetic, genomic, proteomic, electrocardiographic, echocardiographic, neurographic (neural), electroencephalographic, magnetocardiographic, magnetoencephalographic, magnetic resonance (MRI), computer tomography (CT) and X-ray imaging. The results of analysis can be also color-coded, for example, if an indicator is within a normal range or within a certain percent of a moving average of previous values, it will be highlighted with a green color. A borderline parameter can be highlighted by yellow color, and a parameter beyond 3 standard deviations from normal range can be highlighted by red color.

The results of dynamic analysis performed at Scale (level) II are sent to the next, third level of processing. They are also sent to the Level I to personalize (adjust, adapt, individually tailor) the diagnostic thresholds. For example, the threshold for detection of tachycardia can be lowered if the subject's individual heart rate during the last several days was slow. Or the threshold for detection of QT-prolongation could be lowered if the subject is taking antriarrhythmic drugs that prolong QT interval.

When the information is transferred to the Level III, dynamics of each vital sign (primary element, diagnostic indicator) is integrated to generate a combined personalized dynamics that includes changes (trends) of various diagnostic indicators. Combining the information or using parameter fusion (when several parameters are combined into a single, composite parameter) improves the diagnostic value of the information, since a combination of parameters can help to achieve a more accurate diagnosis. For example, combination of trends of heart rate and T-wave alternans can be used to determine at which level of heart rate T-wave alternans increase and at which level of heart rate T-wave alternans disappears. Another example is a combined analysis of changes in heart rate and QT-intervals, which allows determining a personalized relationship between these two values. This combined information can be useful for determining an optimal treatment strategy, for example, whether or not the level of T-wave alternans at a given heart rate is abnormal and should be controlled, for example, by implanting an implantable cardioverter-defibrillator (ICD). The results obtained using this combined analysis at Level III are sent to the higher scale and to the lower scales II and I for individual tailoring (personalized adaptation or adjustment) of diagnostic criteria (thresholds).

At Level IV, the results of information processing performed at lower levels I-III are compared with medical knowledge available in medical textbooks, scientific journals, databases, Internet, networks, and libraries, including statistical data, guidelines, and case studies to determine possible diagnoses. The comparison with medical knowledge can be performed using statistical analysis, pattern recognition, artificial intelligence, neural networks, expert systems, mathematical decomposition, mathematical transformation, or mathematical modeling or computer modeling. As a result of this comparison, a list of possible causes of patient's symptoms is determined along with the probability of each diagnosis. This information is sent to the next, Level V, which determines the most probable diagnosis.

Note that the multi-scale (multi-layer) structure can be compressed into fewer (even 2) scales (that can be implemented in the a single microprocessor, computer, cell phone, PDA, smart phone, microcontroller) or expanded into more scales (which can be also distributed among several different parallel or hierarchical databases connected via network or Internet), depending on the specifics of a clinical setup, available hardware and software resources, and depending on the specifics of an individual patient health status and personal profile, including age, diagnosis, disease stage, etc. It is also possible to use any number or combination of the above-described (or similar) levels (layers, scales). For example, a specific diagnostic structure can be used for subjects with chronic congestive heart failure with a typical profile of a low ejection fraction, a low tolerance to physical activity, relatively high resting heart rate and low heart rate variability. Among the parameters that could be modified for such patients is a narrow range of normal heart rate variations. At each scale, the analysis can use at least one of statistical methods, probabilistic methods, Bayesian models/networks, Markov models or hidden Markov models, pattern recognition, artificial intelligence, neural networks, expert systems, mathematical decomposition, mathematical transformation, or mathematical modeling or computer modeling.

FIG. 2 shows another variant of multi-scale structure, in which the 1st level, low-resolution analysis is implemented together with each diagnostic sensor, so that collecting health data and processing these data in a low-resolution, $1^{st}$ level analysis is done at the same place, in a real-time. The collected heath data and/or the results of $1^{st}$-level processing are then sent to the $2^{nd}$ level processing, possibly, via Bluetooth, other radio-transmitters, cell phone, Wi-Fi or other networks. The $2^{nd}$ level processing, as explained earlier, includes analysis of serial changes, using the information obtained previously from the same subject, and sends the results of analysis back to the $1^{st}$ level to optimize diagnostic and monitoring thresholds.

FIG. 3 shows yet another version of a multiscale structure, in which Scale 2 analysis is also distributed among different locations. The $2^{nd}$ scale analysis can be implemented on-site within the same diagnostic unit that collects health data and performs $1^{st}$ scale analysis. Alternatively, the $2^{nd}$ scale analysis can be implemented at a different physical location, or distributed among several different locations, as FIG. 3 shows.

Note also that the multi-scale structure can be further expanded in horizontal direction, to include different modules of support for different groups of diseases (for example, modules for cardiovascular, neurological, gastroenterological, infectious disease), different patient populations (heart failure, renal failure, chronic obstructive lung disease, elderly, etc.), different groups of medications (anti-arrhythmic, beta-blockers, etc), different device treatments (implantable cardiac devices, hemodialysis, etc.), different medical settings (ambulatory, in-hospital, out-of-hospital, military, mass emergency situations, terrorist threats, weapons of mass destruction alerts).

The multi-scale structure can be implemented in various combinations of computing devices, such as cell phones, specialized processors, personal digital assistant (PDA), smart phone, personal computer, a computer network or specialized networks. It is possible, for example, to implement the first 2 or 3 scales in a miniaturized, personal system (for example, implemented in a cell phone or a personalized monitoring system) that a person carries around, whereas the higher levels are implemented in a computing device that is located remotely and communicates with the lower levels by using wireless communication (cell phone, GPS, GPRS, Internet, Wi-Fi, etc.). Other combinations of scales implemented locally or at remote locations are also possible. Preferably, the higher-level analysis is performed on a powerful computer device, such as a computer server, which has a database of serial data from each subject for comparative analysis, and also a database of medical knowledge of characteristics of different diseases. Another example of implementation of a multi-level structure is a home system, which includes sensors (can be embedded in home appliances, such as bed, chairs); lower and higher-level processing units implemented in a home computer (which can also communicate information to and from an individual via a TV or radio or cell phone) and a higher-level processing (connected via Internet or specialized network) implemented in a medical center. Yet, another example of implementation of a multi-level structure is a car-based system, which includes sensors for physiological monitoring or periodic checkups, (i.e. sensors for monitoring heart rhythm could be incorporated in the armchair; other sensors might be activated and attached to the human body whenever necessary). The sensors are connected with the car's computer (the connection could be wireless, via Bluetooth or Zigbee), so that the computer can perform the $1^{st}$ scale processing or both, the $1^{st}$ and $2^{nd}$ scale processing. Alternatively, the sensors can communicate directly with a cell phone, which performs the $1^{st}$ or $1^{st}$ and $2^{nd}$ scale processing. The cell phone (or the car computer) can be connected wirelessly (via a cell phone, GPS, or Internet) with a remote computer (which contains a database of this person's serial recordings) for a higher-level processing. Each of these processing levels has a bi-directional communication with other levels for exchanging information, individual tailoring of monitored parameters, providing advice or warnings to the individual in the car or sending an alarm/notification to the individual's physician or nurse via a cell phone or remote computer.

The above-described structure can be used for forecasting (prediction) of the trends in patient's status, including forecasting high-risk periods for developing myocardial ischemia or cardiac arrhythmias by analyzing changes in the pattern of physiological indicators and determining periods when these patterns become unusual (for example, exceeding 3 standard deviations of normal range) or abnormal and, therefore, indicating high-risk of a complication, such as myocardial infarction, arrhythmia, or stroke. The prediction can be performed using at least one of statistical methods, probabilistic methods, Markov models, hidden Markov models, Bayesian network, pattern recognition, artificial intelligence, neural networks, expert systems, mathematical decomposition, mathematical transformation, or mathematical modeling or computer modeling.

The above-described system can be also used to provide an advice or a recommendation regarding changes in diet, stress management, physical activity, treatment (for example, administering a drug or implanting an implantable cardioverter-defibrillator or pacemaker device), or a necessity of diagnostic test. The system can also be used for bi-directional communication between individual subjects (patients), medical centers, and medical professionals (physicians, nurses, and technicians). The above-described system can be also integrated into other information management systems, for example, standard data management systems (such as hospital information management systems). The system can represent the results using at least one of quantitative presentation for medical professionals and qualitative presentation for a lay person who has no medical background. Structuring of the analysis is achieved by constructing the at least two, and preferably three, information scales that represent the most significant parameters at different level of detail.

In the practice of this invention, health data is preferably monitored on a substantially continuous, periodic, or quasi-periodic basis, meaning that data are taken or read and recorded periodically such as every few seconds, minutes, hours, days or longer. The periodic recording of data may extend for short periods such as a few minutes or days, or may extend for prolonged periods of time such as weeks, months or longer. The data is generally recorded seriatim or one after another. The data that is recorded may be varied from time-to-time depending on the analysis of data that is collected so as to collect data that may be more relevant to changes in a subject's primary elements. Data is recorded for doing low resolution analysis as well higher scale analyses. As used herein "health data" is used generically to mean all forms of data relating to health, including physiological data that include but are not limited to blood pressure, cardiac output, vascular activity, temperature, respiration, cardiac, abdominal, or breathing sounds, blood flow, hormonal concentration, enzyme and protein levels, genetic, proteomic, metabolomic, and molecular data, neural activity, electroencephalographic activity, and other electrical, mechanic, sonic, biochemical, and biophysical processes in the human body, other information related to human life, including demographic (age, gender), environmental (pollution, job conditions), and psychological data, life styles, exercise activities, etc.

In addition, this invention provides an easy-to-use system for structured and complete analysis and representation of data and its serial changes quantitatively for medical professionals. Structuring of the analysis is achieved by constructing the at least two, and preferably three, information scales that represent the most significant parameters at different level of detail. The multi-scale analysis and representation can be applied to all types of health data defined above. The values of the data obtained from individual patients can be compared with the average values obtained in a group or a population of patients to facilitate analysis of individual data and to determine the values that characterize groups of patients with similar characteristics and/or similar disorders.

A preferred embodiment of this invention further includes implementation of the multi-scale analysis. Specifically, this invention provides for the implementation of the multi-scale analysis on a distributed network of personal devices (which may include devices for registration and processing of electrocardiogram, electroencephalogram, blood pressure, cardiac output, temperature, respiration, vascular tone, blood glucose, and other biochemical, biophysical, biomechanical, hormonal, molecular, and genetic data) and centralized computers with a bi-directional communication between them. This distributed network allows: 1) uninterrupted data acquisition (continuous or discrete) anytime, anywhere, 2) fast transmission of the acquired information to the other computers on the network for processing and comparison with previously acquired serial data (including individual baseline data), 3) fast and accurate processing, analysis, and accurate detection of serial changes, 4) transmitting the results back to personal devices (held by the individuals and medical personnel) to inform them and adjust the monitoring thresholds.

On the network, the data and its processing may be distributed horizontally among the devices and computers according to the computational resources, time period of data acquisition, type(s) of a medical test(s), geographical location, professional and living environment. For example, one distributed personal network of devices and computers could be setup at home, a second network could be setup at a work place, a third network could be setup in a hospital, and a fourth one could be setup in a transportation system (such as a train or an airplane), so that all four networks are connected to each other and can exchange the information instantly. The personal devices may include devices for acquisition and analysis of electrocardiogram, electroencephalogram, electromyogram, blood pressure, impedance, vascular resistance, cardiac output, biochemical, genetic, proteomic, molecular, and other types of health and environmental data.

The advantages of the distributed processing include: 1) a higher computational power and speed of distributed parallel processing, which allow efficient implementation of such computationally expensive methods of artificial intelligence as neural networks, expert systems, and hybrid artificial intelligence systems, and other mathematical and statistical tools, and 2) fast exchange of information among the devices on the network as well as between different networks.

Low, intermediate and high-resolution scales are defined according to the corresponding software and hardware resources. A low-resolution (Scale I) represents a small number of the most important primary elements such as intervals between the heart beats, duration of PQ, QRS, and QT-intervals, amplitudes of P-, Q-, R-, S-, and T-waves. This real-time analysis is implemented in a portable device that requires minimum computational resources. The set of primary elements and their search criteria are adjusted for each physiological signal utilizing computational resources of intermediate or high-resolution levels. At the intermediate-resolution (Scale II), serial changes in each of the said elements are determined using a mathematical decomposition into series of orthogonal basis functions and their coefficients. This scale is implemented using a specialized processor or a computer organizer. At the high-resolution (Scale III), serial changes in all elements of the ECG and their combinations are extracted using orthogonal mathematical decomposition to provide complete information about the dynamics of the signal. This scale is implemented using a powerful processor, a network of computers or the Internet. Scale I may be implemented in a portable, pocket-size device, in which the signal is decomposed into a plurality of primary elements and parameters such as intervals between the heart beats, type of a cardiac complex, amplitudes and duration of P-, QRS, T-, and U-wave, QT-interval, amplitude of ST-segment. Scale I of the system provides the means for real-time electrocardiographic analysis by comparing the primary elements of ECG with reference values (individual thresholds) using the minimum computational resources. The reference values are programmed into the device based on normal values for the primary elements for the patient. Scale I includes means for adjustment of individual thresholds and criteria for rejection of noisy data. A detector of noise and error rejects the noisy data if the primary elements exceed physiologic range. Alternatively, modification of the primary elements and adjustment of their search criteria can be performed automatically at the higher-resolution Scale II or Scale III. In this case, the Scale I analysis is implemented using a programmable microprocessor that can be reprogrammed at the higher-resolution scales to account for the individual characteristics of the physiological pattern and monitoring goals. Specific sets of primary elements can be used for patients with different cardiovascular abnormalities.

Scale I can be used in two modes: static mode and dynamic mode. The static mode is used for one-time ECG examination in which the newly acquired primary elements are compared with the default reference values. The dynamic mode is used for comparison of the newly acquired primary elements and waveforms with the primary elements and waveforms that were previously acquired from the same person. The shapes of QRS, T, and P-waves are compared using cross-correlation function. A small magnitude of the difference between the two measurements permits classifying them as substantially similar and keeping only one measurement in the memory.

Scale I provides sufficient information for standard, one-time, clinical ECG examination. The most significant primary elements may be represented as a color, symbol, or other easy-to-read encoding of indicators that make the results useful and understandable for a lay person and a medical professional. Each signal-indicator corresponds to a single primary element. In the static mode, the values of the indicators are preferably color-coded for a lay person into normal, moderately or severely abnormal. This representation constitutes a static screen. Alternatively, the indicators may be symbol-coded, N for normal and A for abnormal reading; or they may vibrate or produce a sound output for people with vision or hearing impairments. For a medical professional, the indicators provide exact, quantitative values of the primary elements. In the dynamic mode, the indicators are preferably symbol (or color)-coded into C for changed or U for unchanged. This representation constitutes a dynamic screen.

Intermediate-resolution Scale II allows viewing the ECG with automatically determined primary elements on a display and interactive editing of the set of primary elements and their search criteria. The editing can be performed by a user or a medical professional to modify the set of characteristic points or to adjust their search criteria, and can be performed either manually or automatically by the software. The individually adjusted search criteria can then be used to re-program the Scale I analysis as described earlier.

Scale II allows accurate comparison of serial ECGs and detection of small serial changes that may be unexposed by visual inspection of the signals. This scale requires higher computational resources than Scale I and can be implemented in a specialized processor, computer organizer or a personal computer. These computational resources also allow manual entering text information about the patient into the database and specific instructions regarding adjustment of time windows, threshold values, and other variables. To perform the Scale II analysis, the primary elements from serial ECGs are stored into a database to construct the time series for each primary element. The series is decomposed into a few most significant basis functions and coefficients using Principal Component Analysis (PCA) or any other orthogonal set of basis functions. The newly acquired values of the primary elements are compared with the series of the previously obtained values. Furthermore, the changes in the series of PCA coefficients are analyzed to detect small cumulative changes in the dynamics of the series that indicate instability in the cardiac electrical activity.

High-resolution Scale III is used to analyze individual and combined changes in the primary elements; at this scale, the number of the primary variables is increased to include the entire waveform of the cardiac complexes. This allows the most sensitive and accurate detection of the small changes in the individual electrocardiographic pattern. The same PCA approach is used at this scale to expose small serial changes in the ECG recordings. Scale III requires higher computational resources compared to Scale I and Scale II; it may be implemented in a powerful processing unit such as a personal or specialized computer or a distributed network of computers or the Internet.

This invention can be used for one-time examinations by patients, medical professionals, paramedics and lay public, and for dynamic assessment of changes in cardiac electrical activity. The information can be transmitted to an external computer system or a network of computers. For a lay person, the system may also include a database explaining significance of the changes in each primary element and providing simple recommendations about the measures that has to be taken if the readings of the indicators become abnormal. These may include complete cessation of physical activity, contacting a medical professional, taking a medication, etc. More detailed recommendations might be provided for patients who have specific abnormalities or medications. These patients might require special monitoring or individual adjustment of their primary elements. For example, specific monitoring the duration of QT-interval is important in patients taking antiarrhythmic drugs that prolong QT-interval.

The system can be used as:
Hospital or medical center information management;
Information management for ambulatory patients;
Information management for community health program;
Information management for corporate health program;
Self-awareness and health advice system;
Information management for patients with implantable devices;
Medical decision support system for medical professionals implemented on a personal computer, a cell phone, a smart phone, or a personal digital assistant (PDA);
Information management or decision support system that includes personalized analysis of serial data and medical knowledge contained in medical literature and on the Internet;
Personalized advice system implemented on a personal computer, a cell phone, a smart phone, or a personal digital assistant (PDA);
First-aid health-data analyzer for emergency units, paramedics, and medical personnel;
Health data analyzer for a routine medical examination;
A personal one-time or serial data analyzer with storage of individual historic data, adaptive adjustment of individual thresholds and assessment of changes in individual heath pattern;
A one-time or serial health-data analyzer for a group of people, a family or a patient group, with storage of individual historic data for each person, adjustment of individual thresholds and assessment of changes in individual health patterns;
Event-monitoring device including patient-detected events;
Bedside monitoring;
Bedside or ambulatory monitoring providing intelligent alarms to medical professionals when appropriate;
At least one of arrhythmia, stress-test, ischemia, ST-segment, and T-wave alternans monitoring;
Pacemaker and other implantable device checking, bi-directional or uni-directional communication, programming, and control;
Evaluation of the treatment efficacy, side effects and progression of the disease.

Accordingly, an object of this invention is to provide a system for analyzing ECG signals at least at two levels of detail or resolution. Both levels of resolution are presented in simple representation that can be understood by lay persons, as well as medical professionals.

A further object of this invention is to provide an ECG analyzing system that includes a monitoring device for receiving and analyzing ECG signals and which includes means for communicating with an external computer to which the ECG signals can be forwarded for more complex analysis. The monitoring device can be reprogrammed by the external computer to select the primary elements of the ECG signals that are unstable or abnormal. The low level analysis performed by the monitoring device is thus focused on the critical primary elements for that patient.

The system of the present invention can be used for management and analysis of electronic health (medical) records and information, analysis and management of biometric data, or information management of other types of healthcare data.

The system of the present invention provides instant access to information from a variety of distributed sources to reduce costs, improve quality of patient care and optimize decision making. For example, the system can be used to provide a real-time view of in-hospital patient distribution and operations structure in different departments and at different stages of the treatment process, from admission to discharge, or in the Emergency Room. The system can capture and integrate monitoring of vital signs, biometrical data, capture and integrate text, images, technical information related to device functioning and instrumentation status. The system can also provide an intelligent, tailored representation for different types of users and different points of care. For example, it can improve information sharing among the healthcare providers, including physicians, nurses, technicians, clerks, and others. The system of the present invention can also facilitate analysis, management, and optimization of information processing from the traditional departmental systems—e.g., legacy systems (Nursing, Pharmacy, LIS, RIS, PAS, by creating integrated database, applying intelligent analysis and optimizing diagnosis and treatment, including diagnostic and treatment plans and providing intelligent alarms and alerts to support and optimize clinical decision making.

The system of the present invention can collect real-time physiological and health data from a variety of sensors including vital sign monitors, ventilators, infusion pumps. It can also support a wide range of physiologic sensors from a variety of manufacturers. The system can also automatically re-configure itself to accept and recognize new data from physiological sensors whenever a new sensor is plugged into the system. It is also possible to enter new data into the system using an integrated barcode scanning or RFID tag or MEMS tag or other types of automatic entry of information at the bedside in real time. The system of the present invention can also adapt, compare and merge new information with the data that already exist in the system. Because the information flow between different levels/units of the system is bi-directional, the system supports and optimizes seamless exchange of data coming from different diagnostic and treatment modalities, such as patient information from hospital data repositories (e.g., Laboratory, Medication, Admission/Discharge/Transfer and others) and intelligently alert the clinician to potential problems.

The system can also have multiple displays, terminals, including wireless connections with personal handheld devices (PDA, Smart Phones, Cell phones, computers, and computer tablets). Using these displays, users can simultaneously receive different modes of information, such as physiological signal information (vital signs, ECG, blood pressure, cardiac output), real-time intelligent alerts, prescription dispensing, drug interaction, dynamical report, individual patient dynamics, and serial comparison of individual patient's data, etc.

For example, an acute ischemic syndrome (AIS) can be confirmed by measurements of the level of cardiac enzymes (troponins). Since the level of enzymes can be estimated only in a hospital, this information is usually unavailable when the subject is admitted to the emergency room. In the absence of this information, medical decision is made on the analysis of clinical and electrocardiographic signs of ischemia. Yet, this information is incomplete. Thus, the information completeness is estimated relative to the total, theoretically possible, information about a disease state (which is equal to 1), so that the sum of information content (probability estimates, or uncertainty) of all diagnostic tests is equal to 1. The information contained in each test is equal to a number between 0 and 1. At each scale the information completeness (probability of each disease state) can be estimated relative to the complete information (reference) for this disease state. Similarly, the information completeness is also estimated for all scales, relative to the complete, theoretically possible information in all scales.

The probability or information completeness can be represented by the probability transition matrix of a Markov chain, Bayesian probability, probabilistic neural network, or some other non-probabilistic matrices and methods. Traditionally, the term "multiscale analysis" or "multi-resolution analysis" refers to either (1) a spatial multiscale analysis (distributing analysis of complex structures or processes that span different spatial scales, for example, molecular-cellular-organ-body scales of biological processes into several spatial scales), or (2) a temporal multiscale analysis (distributing analysis of complex, dynamic processes that involve several different time-scales). The term multiscale analysis used herein refers to the temporal multiscale analysis adapted to serial (longitudinal) data or a combination of temporal and structural multiscale analysis adapted to serial (longitudinal) data (because serial images, image information, and other data spanning different spatial scales can be also included in the analysis). Note that the traditional temporal multiscale analysis refers to an application of a mathematical formula or function (for example, a wavelet function or a nonlinear function, such as entropy), to different time-scales by varying a time-window parameter (i.e., using a mathematical translation or dilation of a function). A detailed description of a multiscale wavelet analysis can be found in The Statistician (2000) 49, Part 1, pp. 1-29 (Abramovich F, Bailey T C, Sapatinas T. Wavelet analysis and its statistical applications.). 5 A description of a multiscale entropy analysis can be found in Physical Review E 71, 2005, pp. 0219061-02190618(Costa, M, Goldberger A L, Peng, C.-K. Multiscale entropy analysis of biological signals). In this approach, the fundamental mathematical function remains unchanged at all time scales, but the scaling parameters change. Our multiscale approach, presented herein and in my previous US10 Patents. No. 6,925, 324, and 6,389,308), incorporated herein by reference, is different from the traditional methods for multiscale analysis described above (in some respects, it can be viewed as a non-trivial generalization of the traditional multiscale and multi-resolution approaches). It allows 1) usage of different mathematical, pattern-recognition, statistical, probabilistic, artificial intelligence functions/models/estimates/approximations at different time scales, 2) usage of a single time-point (snapshot) compared against reference values at the 1st scale of analysis (this snapshot analysis can be performed one-time, periodically, quasi-periodically, or continuously) and multiple time-points (serial data) at the higher-scales of analysis, 3) usage of composite functions and estimates obtained by combining different parameters and time-scales at higher level analytical scales, 4) bi-directional exchange of information between different scales to improve the analysis. Using recently introduced terminology, our multiscale analysis approach can also be viewed as a non-trivial extension, improvement, and generalization of a recursive projection method (Shroff G M, Keller H B. (1993) SIAM J. Numer. Anal. 30, 1099-1120) that can be also adapted for "equation-free modeling" (Theodoropoulos C, Qian Y-H, Kevrekidis I G. PNAS (2000) 97, 9840-9843) of multiscale, complex processes.

FIG. 4-7 show various implementations of the multi-scale, network-distributed processing and display of physiological information on mobile devices.

Magnetic-Resonance Imaging Applications

Magnetic-resonance (MR) imaging allows clinicians to obtain information about internal organs without using ionizing radiation. However, it also creates electromagnetic interference due to the presence of strong and variable electromagnetic fields (e.g., magnetic-field gradients and radiofrequency (RF) pulses), which generate interference with physiological measurement equipment, such as an electrocardiogram. The electromagnetic interference (EMI) complicates the task of collecting high-quality physiological data (e.g., diagnostic ECG, pulse oximetry, and blood pressure waveforms) and requires filtering of MR-generated noise.

This invention extends the principle of common mode rejection, which is known in signal processing, for the MRI-specific environment and adaptive, multi-scale, distributed processing. This principle is used for rejecting the components of input signals that are common to two input leads (sensors) by subtracting the two signals. It is widely used in differential amplifiers and other devices for filtering out external noise. One particular application of this principle is commonly used for filtering the power-line interference when two signals are recorded from the same or similar locations, and presumably, receive the same amount of power-line interference. However, this principle has not been used for filtering MR-related interference, specifically, for filtering the effects of gradient magnetic fields (eddy currents) or radio-frequency pulses generated in the physiological data, because of the additional complexities and constraints imposed by the MR-environment; specifically, the presence of several electromagnetic fields (static field, field gradients and radiofrequency pulses). Due to these complexities, it has been commonly accepted that the number of leads needs to be reduced to a minimum to minimize the interference and eddy current effects. For these reasons, no attempts have been made to apply the common-mode rejection principle, which requires additional (reference) signals. It has been also commonly accepted that the MR-generated interference makes high-fidelity recording of physiological signals (such as diagnostic-quality electrocardiogram) not feasible. Therefore, no attempts have been made to develop high-fidelity filtering approaches for such data in the MR-environment.

This invention provides the method to filter MR-specific noise without degrading the quality of physiological signals (such as an electrocardiogram) by using some of the information from the signals obtained at the same or similar location (as a reference) and subtracting this reference information from the physiological signal. Because MR-generated interference is spatially specific (due to the presence of magnetic field gradients, inhomogeneity of the electromagnetic fields and RF pulses), this method provides superior accuracy for filtering the noise from physiological signals compared with currently available methods.

The principle of operation of this invention is illustrated in FIG. 8. It shows implementation of present invention for magnetic-resonance imaging and filtering electromagnetic interference generated by the MR-scanner from physiological signals, such as an electrocardiogram, electroencephalogram, blood pressure, transthoracic impedance, cardiac output, blood pressure, temperature, respiration, and oxygen saturation waveforms. From each location of the patient's body, the system collects a pair of signals; a physiological signal (contaminated by the EMI generated by MR-scanner) and a local reference signal, which contains only EMI generated by the MR-scanner, including gradient magnetic fields and radio-frequency pulses. By subtracting the local reference signal from the physiological signal at each location, the system of present invention filters the MR-generated EMI from physiological signals.

As shown in FIG. 8, the system receives signals from sensors (S1, S11, S2, S22, S3, S33, and so on) located at various sites on the surface of the patient's (subject's) body. At each site, a physiological-recording sensor (S1, S2, S3, and so on) is attached to the patient's body and records a physiological signal, whereas a local-reference sensor (S11, S22, S33, and so on) is not directly connected to the patient's body and records only electromagnetic interference generated by the MR-scanner (gradient magnetic fields and radio-frequency pulses). There are a number of possible configurations for the pair of physiological-recording sensor and local-reference sensor. In one configuration, the local-reference sensor is a separate sensor whose location (and cable) is adjacent to the physiological recording sensor, as shown in FIG. 8. For example, in case of an electrocardiographic (ECG) or electroencephalographic (EEG) recording, the physiological-recording sensor can be connected to the patient's skin using an MRI-compatible, off-the-shelf ECG or EEG electrode, whereas the local-reference sensor is covered by a plastic insulator, which prevents direct contact with the patient's skin. Alternatively, the pair of local-reference and physiological recording sensors (and their respective cables) can be housed together under a single insulating cover, with the physiological-recording sensor having an open connector (e.g., snap or pinch) for attaching the recording electrode and the local-reference sensor being completely covered by insulating plastic.

The sensors are connected to the data collection module, which may incorporate a differentiator unit, which subtracts local-reference signals from the physiological-recording signals (FIG. 8). The differentiator can be implemented using a differential amplifier or a differential, conditioning and filtering circuit, which performs additional filtering and conditioning of the signals. The data collection module also has a communication unit, which is preferably, wireless. It receives commands from and transmits signals to the receiving station via Bluetooth, Wi-Fi, Zigbee or some other wireless communication protocol.

The multi-level analysis is distributed between the data collection module (DCM) and receiving station with bi-directional communication between them. The receiving station sends commands that program, control and adapt the DCM operation for specific, user-determined conditions. The DCM receives commands and adjusts its operations accordingly. The adjustments may include sampling rate, signal resolution, communication frequency, selection of real-time processing, compression and filtering options, as well the utilization and size of the data buffer for sending data to the receiving station. The receiving station adapts its data-receiving buffer for the presence (or absence) and data size in the DCM buffer to achieve uninterrupted and substantially continuous data transmission and display on the screen of receiving station in a near real time.

The adaptive algorithm runs on a receiving station (FIG. 8), which performs either Scale-1, Scale-2 or Scales 1 and 2 processing. It also displays filtered and/or raw data for user to review. The data acquisition unit, which connects to the sensors (S1, S11, S2, S22, S3, S33, and so on), communicates with the receiving station wirelessly or using cable communication. The firmware in the data acquisition unit adapts the Scale-1 processing (turns the subtraction ON or OFF) according to the commands (adaptation parameters) received from the data-receiving station. These adaptation parameters, in this case, is the information sent from Scale-2 processing on the receiving station back to the Scale-1 processing on the data acquisition unit.

The data-receiving station can be implemented on a mobile device or can be linked wirelessly with personal mobile devices (smart phone) displaying the data for a user. In the latter scenario, the data-receiving station performs Scale-2 processing, compression, filtering and/or condition of the data and sends these compressed and/or conditioned data to the mobile device implementing Scale-1 for user's review. The data-acquisition unit is located inside the MR-room, whereas the data-receiving station can be located in the MR-room or in the control room. The invention also provides for higher-scale integration (fusion) of the MR-data with other imaging modalities (e.g., X-ray), video generation (cine) and integration with other physiological data. Specifically, the data processing in the data-receiving station can be adapted to incorporate higher-level processing, which includes physiological information from several signals (Scale-3 analysis). Results of the Scale-3 processing can be the adaptation parameters sent to Scale-2 processing on the data-receiving station and/or Scale-1 analysis on the data acquisition unit. The results of the Scale-3 processing consist of compressed and/or filtered waveforms (which can be buffered) and parameters from multiple signals, adaptation thresholds/parameters and feedback messages to users. This information is transmitted back to Scale-1 and Scale-2 processing to tailor the processing and to provide fast and efficient viewing of compressed waveforms for the users on mobile devices.

Although most examples herein are related to the field of medical monitoring, other applications of this invention are obvious for those skilled in the art.

BRIEF DESCRIPTION OF THE DRAWINGS

A full understanding of the invention can be gained from the following description of the preferred embodiments when read in conjunction with the accompanying drawings in which.

DESCRIPTION OF THE PREFERRED EMBODIMENTS

Figure 1:
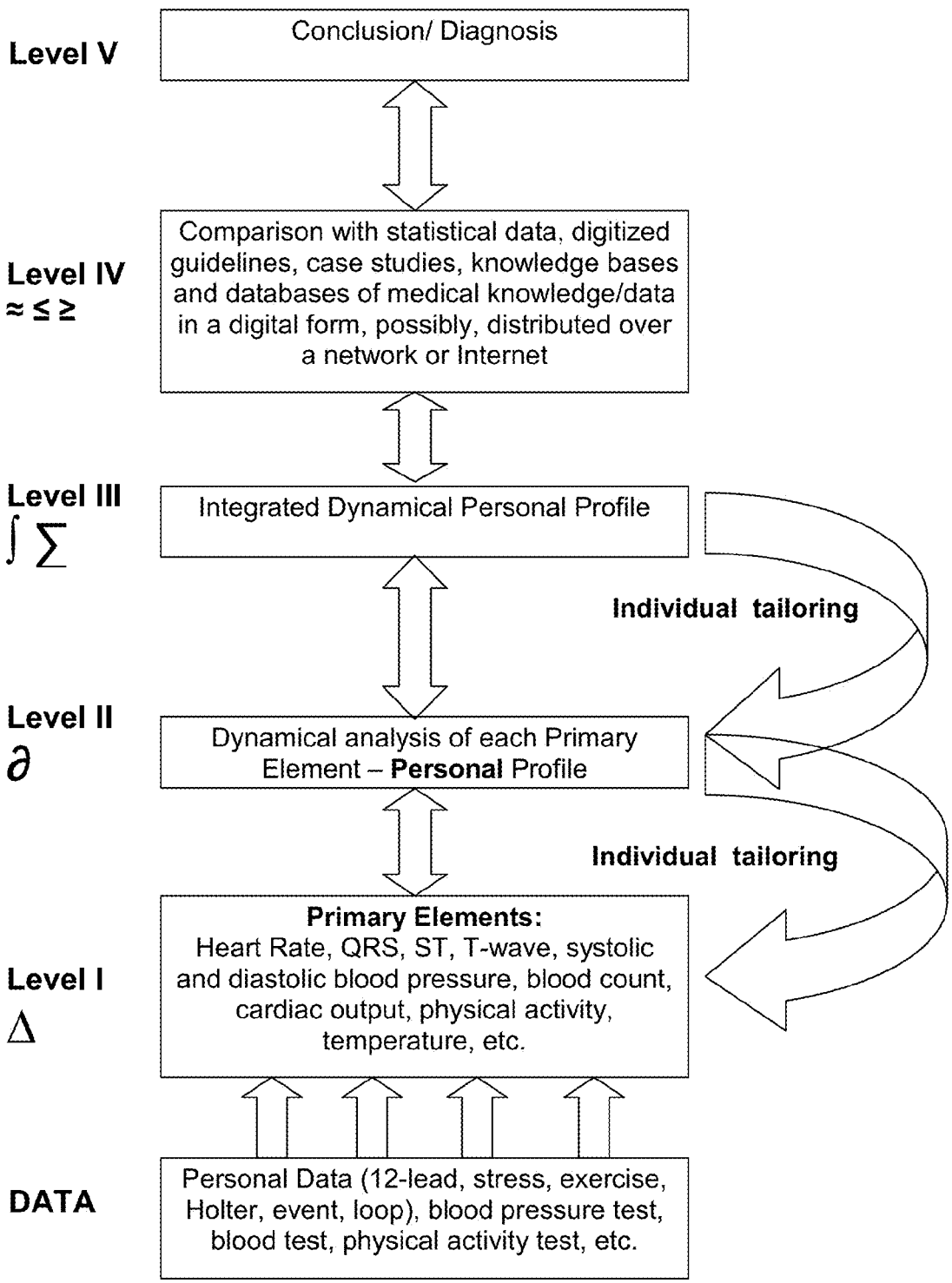
FIG. 1 is a flow chart of multi-scale analysis and representation of health data in accordance with this invention.
Figure 2:
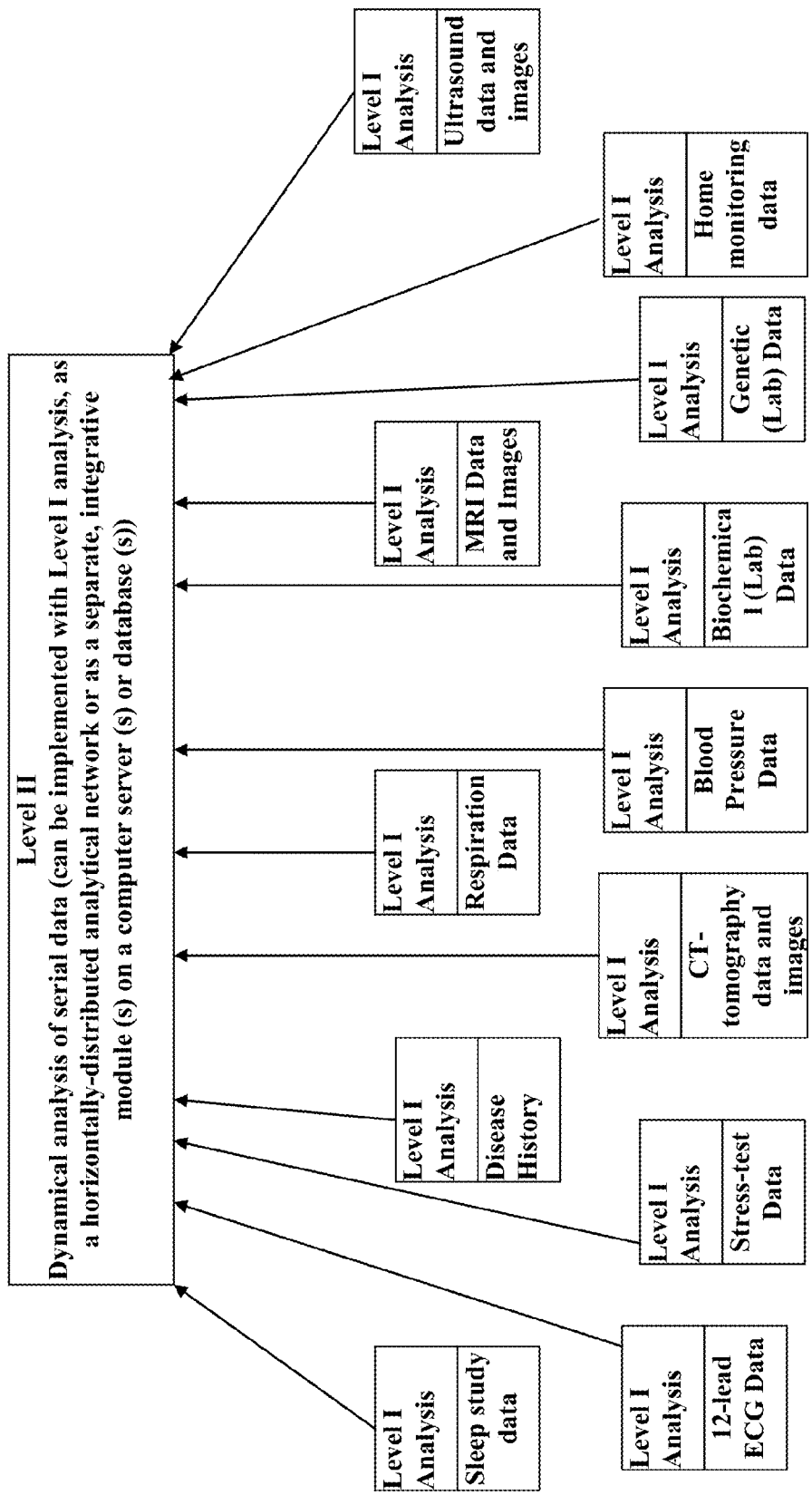
FIG. 2 is a flow chart showing horizontally and vertically distributed multiscale analysis and representation of health data in Levels I and II (with horizontally distributed Level I analysis).
Figure 3:
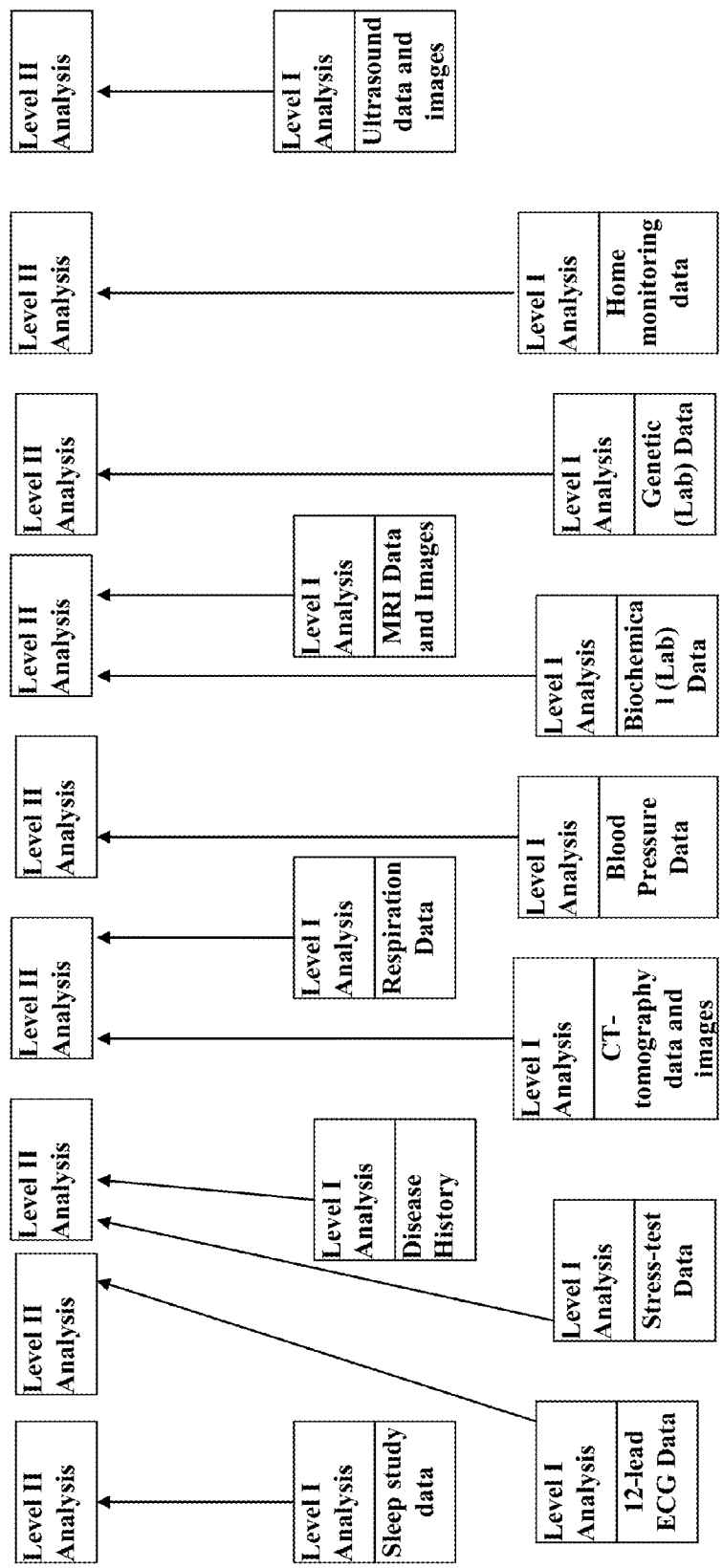
FIG. 3 is a flow chart showing horizontally and vertically distributed multiscale analysis and representation of health data in Levels I and II (with horizontally distributed Level I and II analyses).

FIGS. 4-7 show four possible configurations of the PELEX (trademark of PinMed, Inc.) system which implements the main principles and know-how of network-distributed data processing using an electrocardiogram (ECG) as an example of physiological signals. The overall concept of the system is to provide a software and hardware platform for physiological monitoring, analysis of serial changes, and wireless communication between patients and medical professionals anytime, anywhere. The smart phone/PC/computer tablet acts as an intelligent interface to collect physiological data; analyze and display vital information; and transmit it onto a remote server/cloud for detailed analysis of serial changes. The result of this analysis could be sent to the physician's and/or patient's smart phone to view the data in real time or close to real time, alert medical personnel and provide appropriate feedback to the patient. In addition to ECG, the PELEX system can be also used for collecting, transmitting and processing data for electroencephalogram, blood pressure, respiration, temperature, glucose level, physical activity, oxygen saturation, body position, cardiac output, peripheral resistance, pulse transit time, pulse wave velocity, pulse wave amplitude and other physiological signals.

In Configuration 1 (FIG. 4), the data are collected using PELEX VITALS (trademark of PinMed, Inc.) data collection module (DCM), which communicates via Bluetooth with a smart phone. The PERSONAL HEART EXPERT program (trademark of PinMed, Inc.) is installed on the smart phone in one of the two configurations, PERSONAL HEART EXPERT PT (for patients) or PERSONAL HEART EXPERT MD (for medical professionals), as described below. This program sends commands to the DCM, sets data recording and transmission parameters and receives data from DCM in real time. The PERSONAL HEART EXPERT program can be configured to plot data on the display of a smart phone in real time, perform first-level processing/compression and communicate with the PELEX SERVER software (trademark of PinMed, Inc.) installed on the network server, computer or Internet server (cloud). The PELEX SERVER software performs second-level and possibly higher-level processing. The results of this analysis are then used for the following purposes:

1) The PELEX SERVER can be configured to automatically send information/parameters for adjusting the first-level processing back to the PERSONAL HEART EXPERT program installed on the smart phone (FIG. 5).
2) The PELEX SERVER can be configured to automatically send processed/compressed data and numerical results (which can be color coded) to another smart phone (mobile device) running the PERSONAL HEART EXPERT MD program for display and review by medical professionals (FIG. 4).
3) The PELEX SERVER waits for a connection from authorized users from remote computing devices with the PELEX HEART EXPERT MD program installed on their computers and/or smart phones (FIGS. 4-7). When such users connect to the PELEX SERVER using the PELEX HEART EXPERT MD program, they can quickly display and review the data and results of analysis in numerical and/or graphical form (which can be color coded) on the screen of a computing device (cell phone, smart phone, tablet or computer).

Figure 4:
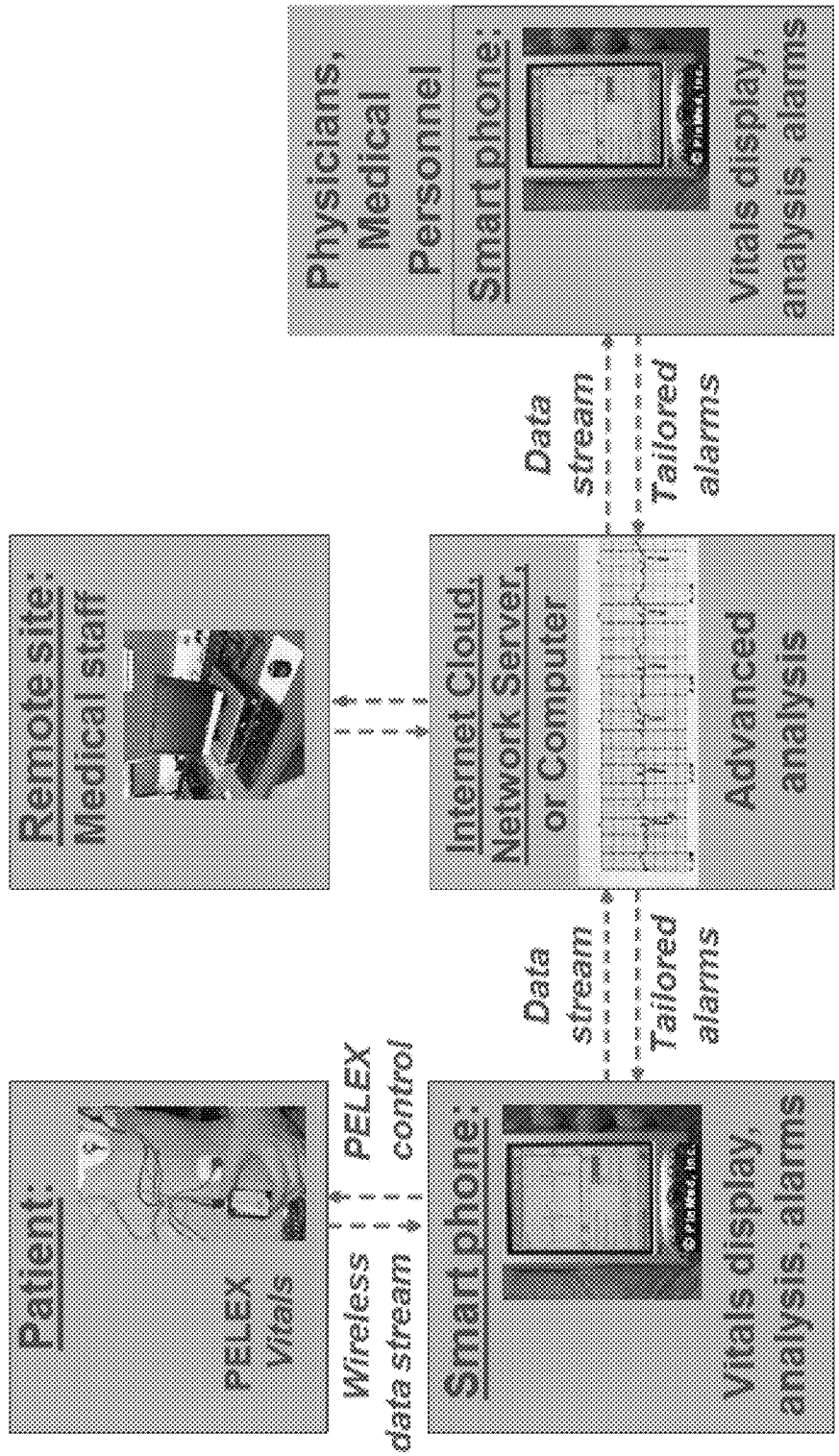
FIG. 4 is a diagram of one specific implementation of the multi-scale, network-distributed processing and display of physiological information on mobile devices.
Figure 5:
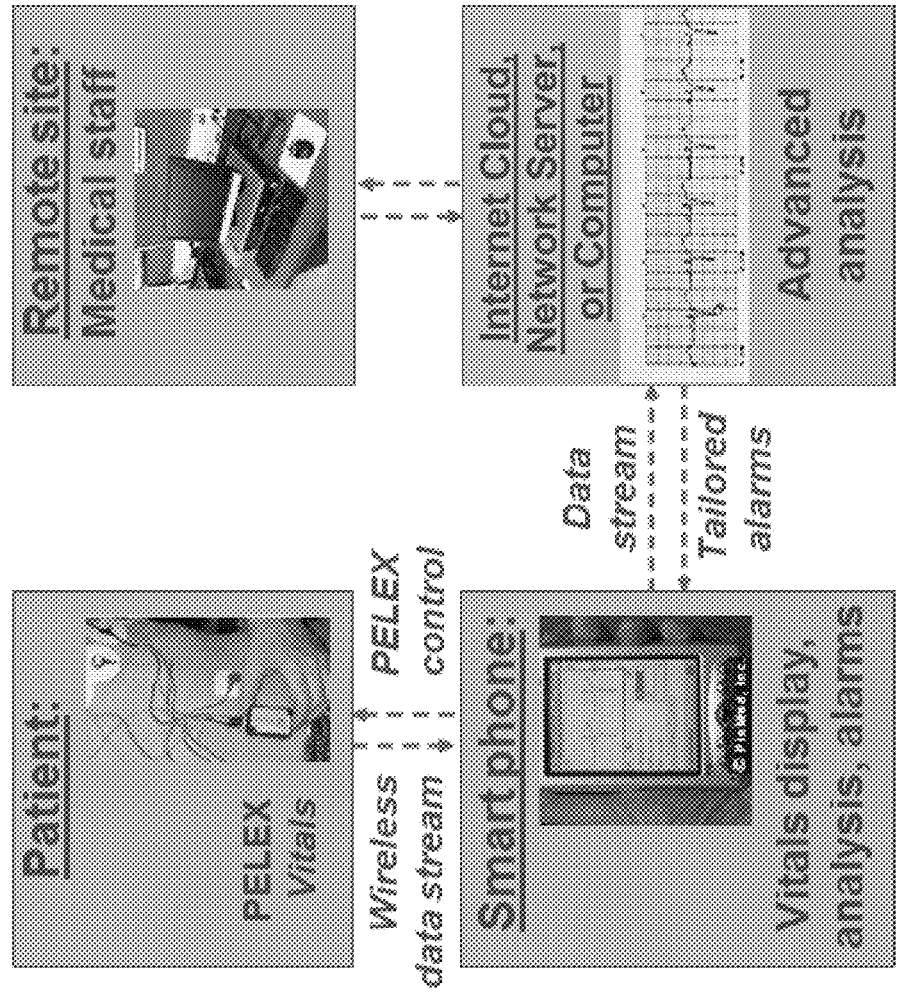
FIG. 5 is a diagram of a $2^{nd}$ specific implementation of the multi-scale, network-distributed processing and display of physiological information on mobile devices.

The architecture and general structure of the PELEX HEART EXPERT MD and PELEX HEART EXPERT PT configurations are similar. They include the same or similar modules for data receiving and buffering, plotting/displaying in real time (or close to real time), as well as plotting/displaying of historical (previously recorded) data, scrolling the data back and forth in time, zooming in and out, as well as other standard, graphical user-interface (GUI) functionality. As shown in FIG. 4, both configurations use the same general layout of the data display, windows, axes, grids, scroll buttons, time stamps and so on. Data buffering is also used in both programs to improve user experience with the data display/plotting, providing smooth, substantially continuous plotting of signals on the screen with the speed of real-time data streaming (or other, user-defined speed). The size of the circular buffer for temporary storage of received data could be adjusted according to the required time delay (proportional to the buffer size) between the time when data are received and the time when the data are plotted on the screen, the size and resolution of the local display (which can be different for different types of cell phones, smart phones, tablets and personal computers), as well as user preferences. Using such a buffered operation, the delay between the time when data are received and the time when data are plotted usually does not exceed a few seconds.

The differences between the two configurations are primarily related to the levels of functionality, data processing, analysis and presentation/display. The PELEX HEART EXPERT PT receives data from the PELEX VITALS data recording module (DCM) via Bluetooth wireless link, as shown in FIG. 4, whereas PELEX HEART EXPERT MD can receive the data from either PELEX VITALS data recording module via Bluetooth wireless link or the PELEX SERVER (installed on a network server or Internet server/cloud) using an Internet connection via a wireless cell-phone line or computer cable. The PELEX HEART EXPERT MD also provides display of waveforms and its detailed analysis, which includes numerical values, diagnostic text statements and graphs. The analysis is performed using one or several (consecutively applied) plug-and-play analysis modules, which interface with the main PELEX HEART EXPERT module via a common input-output data format and interface. Different analysis modules have been developed and interfaced with PELEX HEART EXPERT program for different categories of patients and/or diseases, for example, modules for analysis of arrhythmias, for diagnostic analysis of 12-lead electrocardiogram, for analysis of blood pressure wave and trends, for analysis of pulse oximetry signal and oxygen saturation. In contrast, PELEX HEART EXPERT PT application does not provide detailed medical summary or numerical results. Instead, it provides simple feedback messages for the patient (described below) and a simple interface with the PELEX VITALS data collection unit allowing data collection, testing data quality, saving and transmission to the PELEX SERVER.

Figure 6:
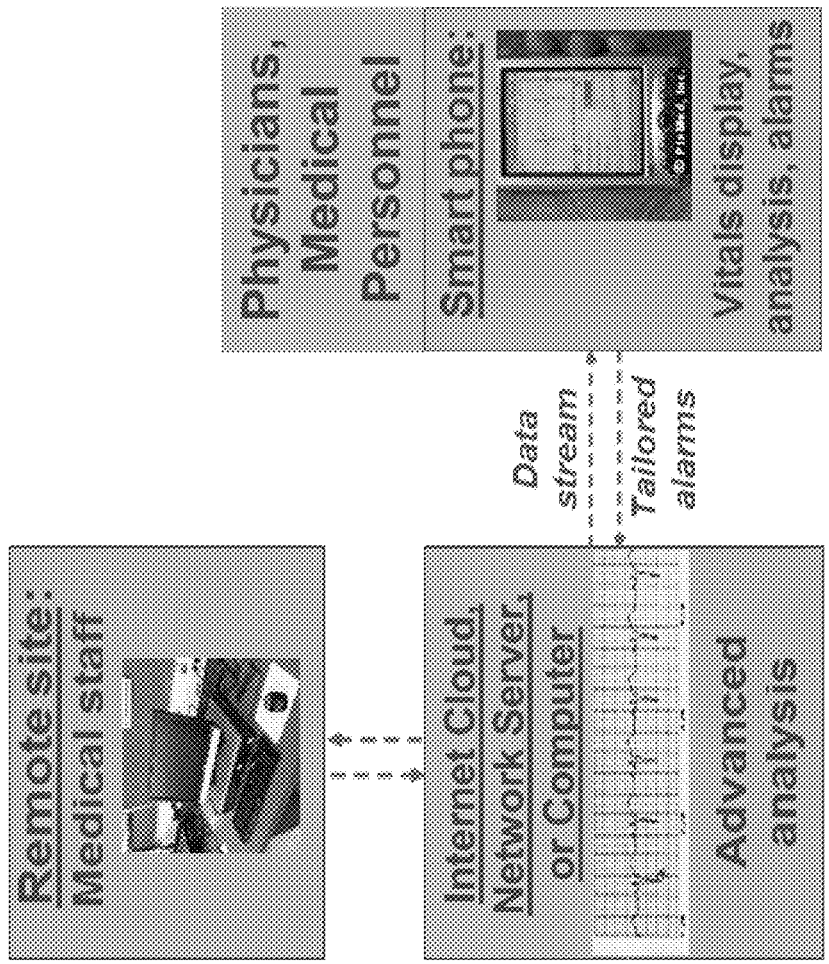
FIG. 6 is a diagram of a $3^{nd}$ specific implementation of the multi-scale, network-distributed processing and display of physiological information on mobile devices.
Figure 7:
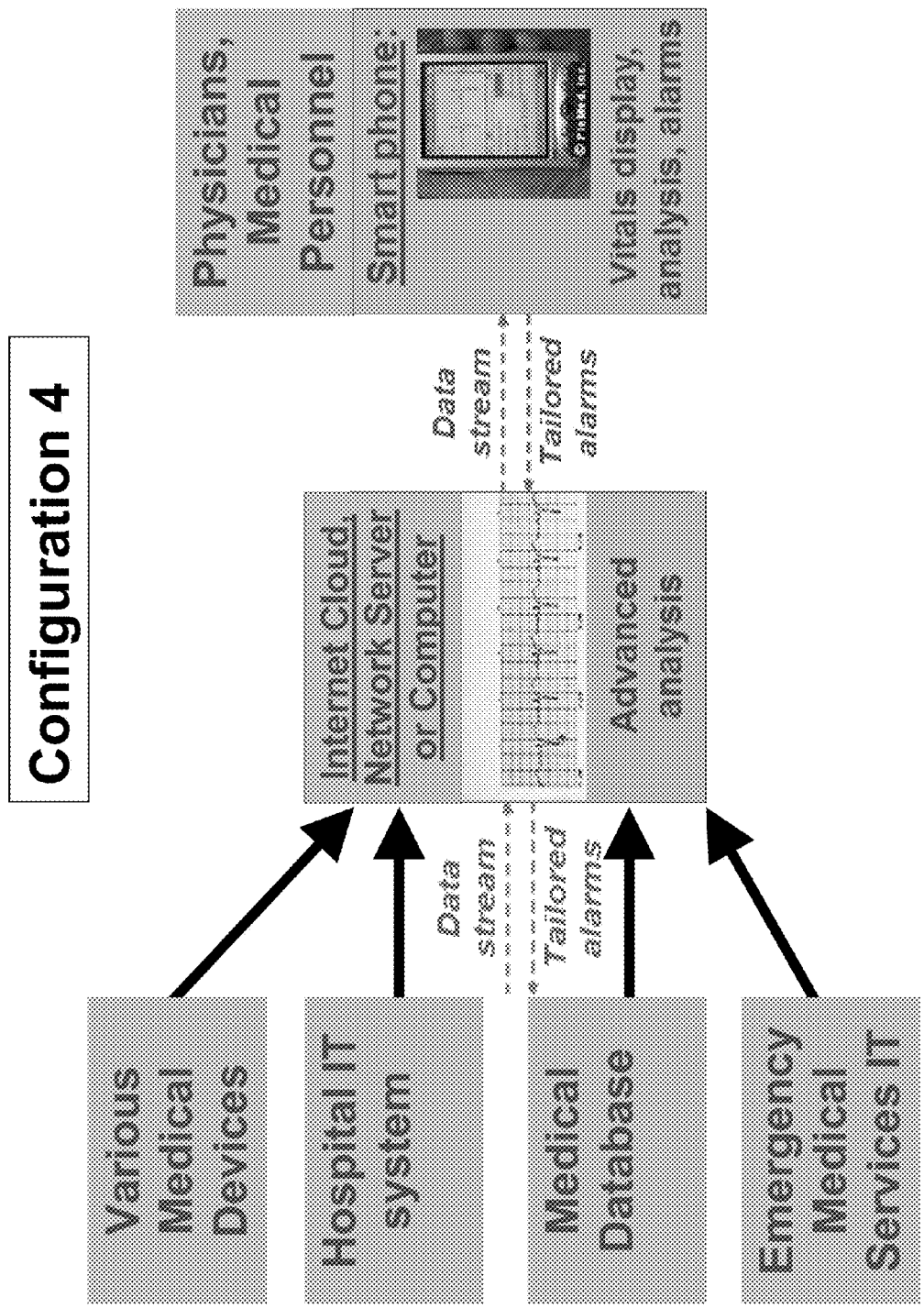
FIG. 7 is a diagram of a $4^{th}$ specific implementation of the multi-scale, network-distributed processing and display of physiological information on mobile devices.

FIGS. 6 and 7 show PELEX system configurations, in which data are transferred to the network server or Internet server (cloud) running PELEX SERVER from various types of medical devices (instead of the PELEX VITALS) and streamed to the physicians' smart phones running PELEX HEART EXPERT MD software.

The specific modules of the PELEX system and their features include:

I. The all-in-one, miniature, wireless data collection module (DCM), which allows virtually any type of ECG examination, tracking physical activity, body position, blood pressure, pulse oximetry, electroencephalogram and other information. In particular, the recorder allows high-resolution (1 microvolt) recording of 1-12 ECG signals at 100 to 1000 Hz sampling frequency and can work as a gold-standard, 12-lead ECG system, stress-test ECG, Holter or event monitor for long-term (hours to weeks) monitoring. The miniature size is important for users (medical professionals and patients) because it makes the system more convenient to carry (for a medical professional) and allows the patient to use it during regular daily activities and during sleep without disrupting regular life and without being visible to other people. The DCM is "paired" with a smart phone or PC or a computer tablet to allow secure connection via Bluetooth communication protocol. The signals are then transmitted from the DCM to the paired smart phone/PC/tablet for processing. The smart phone/PC/tablet immediately processes the recorded signals using, for example, an arrhythmia-detection program or some other "plug-and-play" processing module. The information is stored locally, and can be seamlessly transmitted over the Internet to the Internet server/cloud using any type of Internet connection (a cell-phone communication link, a wireless modem, a dial-up modem, LAN, or Wi-Fi).

II. Cloud/network server PELEX SERVER software receives the incoming data; performs data compression, filtering, and conditioning (rectification), as well as complete morphological analysis, including analysis of the electrocardiographic amplitudes and intervals between P, Q, R, S, and T peaks, QT, PQ, QRS-durations, and ST-intervals; records the results to a database; and immediately transmits the compressed and filtered waveforms, as well as numerical results to the physician's smart phone (or personal computer) running the PELEX HEART EXPERT MD software. The physician can review the compressed and processed waveform and parameter data in real time or close to real time on the smart phone's display. At the same time, the PELEX SERVER software automatically sends to the patient's smart phone running PELEX HEART EXPERT PT a simplified statement, such as "Your ECG is being analyzed. No changes have been found. You can resume your regular activity" or "Your ECG is being analyzed. Please stop all physical activity. If changes are found, you will be notified about the results shortly." In addition, the information is color coded green, yellow, or red to make it understandable for a layperson. The PELEX SERVER software can be configured in such a way that if the processing algorithm determines changes or abnormalities, the information, including compressed physiological data and medical summary of analysis, is automatically transmitted to the physician's smart phone. In addition, the PELEX SERVER software can be configured to perform pattern-recognition based (individually tailored) processing, compression, filtering and analysis of serial data to detect subtle but clinically significant changes and abnormalities that escape detection by visual inspection or standard analysis. The advanced serial analysis determines individually tailored monitoring thresholds and alarms that are automatically transmitted to the patient's smart phone to improve accuracy of analysis of future data. For example, individually tailored monitoring thresholds may include those for heart rate (bradycardia, tachycardia, pause), electrocardiographic ST-interval (the threshold for detecting ischemia) or QT-interval (the thresholds for determining QT-prolongation). In addition to the electrocardiogram, the tailored monitoring thresholds can be also used for other signals, including blood pressure, heart rate, oxygen saturation, respiration, body position (to diagnose an episode of syncope or fainting), glucose level, electroencephalogram, transthoracic impedance, cardiac output, vascular resistance and other signals.

III. The PELEX HEART EXPERT MD software allows connection to the server over the Internet (or other type of network) from a computer, cell phone (smart phone), or computer tablet, fast and efficient display of physiological data on the screen, as well as editing, correction, and verification of results of analysis. The program also allows adjustment of the data monitoring thresholds for each individual patient. The adjusted thresholds are saved in the PELEX DATABASE (on the network/Internet server) and automatically transmitted to the patient's smart phone, running the PELEX HEART EXPERT PT software (in which the thresholds are updated automatically).

Some Intended Uses and End Users of the PELEX System

1) Portable 1- to 12-lead ECG recorder for medical professionals, including cardiologists, internists, nurses, ECG technicians, emergency medical service (EMS), and other medical personnel.
2) Long-term, ambulatory ECG monitoring, including Holter and event monitoring for patients with a history of arrhythmias, coronary artery disease, syncope, and other patients referred for this type of testing by the physicians.
3) Stress-test ECG for patients with coronary artery disease.
4) Short-term, serial ECG examinations for patients with chronic cardiovascular disease, such as congestive heart failure, who require periodic checkups to optimize treatment and prevent complications.
5) Blood pressure monitoring.
6) Monitoring physical activity and changes in body position to detect syncope (fainting).
7) Monitoring respiration, sleep time and quality, sleep-disordered breathing, and sleep apnea.
8) Monitoring oxygen saturation.
9) Monitoring arterial-pressure wave, arterial wave amplitude, duration, morphology and other characteristics.
10) Monitoring transthoracic impedance, edema, cardiac output and peripheral resistance.
11) Monitoring blood and/or urine glucose level.

System Overview Using an Example of ECG Recording

The ECG electrodes (2 to 10 electrodes are required for 1- to 12-lead recording, respectively) can be attached to the patient's chest in standard locations; the recorded signals are transmitted to the smart phone wirelessly (Bluetooth protocol). The smart phone running PELEX HEART EXPERT program (in the "PT" or "MD" configuration, as described above) presents a simple interface to 1) set up and configure the protocol as detailed below; 2) initiate/stop local ECG monitoring; 3) transmit ECG to the server via Internet using a cell-phone line, wireless modem, a dial-up modem, LAN, or Wi-Fi router; 4) display recorded ECG signals; and 5) display results of ECG analysis. The smart phone also transmits the ECG data to a remote server via a wireless link to perform advanced processing, compression, filtering and/or analysis, as well as to determine serial ECG changes. To perform this analysis, the PELEX SERVER software automatically finds in its database all ECG recordings from the same patient and compares the most recent recording with the previous ones. The results of this analysis alone with the ECG signal are sent wirelessly to the clinician's smart phone running PELEX HEART EXPERT MD software. At the same time, the PELEX SERVER software also sends back wirelessly to the patient's smart phone 1) adjusted values for individual's monitoring parameters, and 2) appropriate information for the patient. In addition, an individual's monitoring parameters can be adjusted in the PELEX SERVER software (using the PELEX HEART EXPERT MD software for communicating with the PELEX SERVER) and automatically sent to an individual's smart phone running the PELEX HEART EXPERT PT program (application).

The PELEX HEART EXPERT PT Software Processing Functions

The PELEX HEART EXPERT PT software on a smart phone compresses the data into a small set of the most important parameters (primary elements) from the incoming signals, including compressed and filtered waveforms, amplitudes and time intervals, for local display purposes. It also compresses the information for onward transmission to the remote cloud/server, reducing the transmission time and battery drain in the smart phone. Additionally, the software extracts the information coming back from the remote server to 1) adjust the parameters for monitoring primary elements, and 2) graph serial changes or display other forms of patient-specific feedback.

Display and Alarms

Once the PELEX HEART EXPERT software on a smart phone is configured with the above options (in either "MD" or "PT" configuration, as described above) and a link is established with the DCM, the system runs automatically with little or no user intervention. The local display indicates:
  a) Status of the DCM (Bluetooth link within range and transmitting successfully),
  b) Whether the unit is in active recording session,
  c) Whether the unit is transmitting to a network server/Internet server/cloud,
  d) Battery life status in the DCM (this information is contained in the data packet),
  e) Battery status on the smart phone,
  f) Feedback from the remote server, including compressed data and results of physiological data processing, including parameters derived from previous recordings, normal values and the trends over the last N physiological recordings, where N is an integer number of records selected by the user or preset in the software configuration.

Smart Phone—Cloud Communication

The smart phone running PELEX HEART EXPERT program (in either "MD" or "PT" configuration, as described above) establishes a connection with the remote server specified in the configuration data. If the connection is successful, the smart phone passes data onto the remote server and then looks for information coming back from the server/cloud.

The PELEX HEART EXPERT MD Software on a Physician's Smart Phone

A physician's smart phone receives the patient's physiological information from the cloud (allowing physicians to monitor patient information remotely, while the patient is located at a hospital, at home, at the point of care, or on the road). Because the information (physiological waveforms and extracted parameters, such as heart rate and blood pressure) has been compressed and filtered on the cloud, the physician can view the data on the smart phone's display with the speed and convenience of real-time data streaming, zooming in/out, and scrolling data back and forth in time (viewing historical data) without any time delays.

Network Server (Cloud) Processing, Display, and Transmission to the Smart Phone The PELEX SERVER software working on a remote network server, Internet server/cloud performs processing, compression, filtering and analysis of physiological data, including analysis of serial changes and multiparametric analysis of several signals/data streams (fusion of data from several data sources), individual adjustment of the monitoring parameters that are transmitted back to the patient's smart phone. The server also transmits physiological data and results of serial analysis to the clinician's smart phone. The following is a list of the required elements of the PELEX SERVER software.

The PELEX SERVER Software on a Network Server/Internet Server/Cloud

1) The PELEX SERVER software processes requests from multiple smart phones (running PELEX HEART EXPERT software in either "MD" or "PT" configuration, as described above), establishes multiple simultaneous connections, retrieves from the database physiological data for each individual patient (including serial recordings obtained at different time points), performs serial analysis, and stores the information in the PELEX DATABASE (trademark of PinMed, Inc.) for future reference; the PELEX DATABASE software can be also installed on the same networks server where the PELEX SERVER is located or it may be installed on another network server, or distributed among several servers on the network/cloud.

2) Once a session is established with a smart phone, the incoming physiological data is immediately processed, compressed and filtered automatically, for example, to verify location of the electrocardiographic fiducial points, including P, Q, R, S, and T-peaks, and primary elements. Next, serial analysis is performed using a mathematical transformation, such as a linear orthogonal decomposition, with minimal time delay. The following parameters are set up prior to the analysis: adjustable time windows, window overlap, and the number of eigenvectors used.

3) All active sessions are listed with the patient ID. At any time point it is possible to select an individual's incoming physiological data and view it in real time along with the results of the above analysis.

4) The server also sends compressed waveforms and results of the serial analysis to the clinician's smart phone for viewing these compressed signals and changes in most important parameters (e.g., heart rate) on the smart phone in real time or close to real time. Continuous streaming of real-time data and user-adaptive viewing (such as scrolling and viewing historical data, zooming in and zooming out) is enabled by transferring compressed data over the network to minimize the time delay and buffering compressed waveforms on the smart phone for substantially continuous (uninterrupted) display.

5) The server can also be configured to send updated monitoring parameters back to the patient's smart phone. These parameters are derived from serial physiological data to represent an individual's range of variations in the primary elements. Adjustment of these individually tailored parameters in the PELEX HEART EXPERT PT on the patient's smart phone personalizes monitoring thresholds and improves the accuracy of real-time tracking and quantification of serial changes.

Viewing Tools

1) Waveforms, including raw, compressed, and filtered signals.
2) Simple graph, such as ECG with R-peaks marked.
3) Trends of the serial changes in the primary elements. The normal range, maximum and minimum thresholds should be marked by different colors (green=normal, yellow=borderline [close to the thresholds], red=abnormal [exceeds the threshold or range]).

The PELEX system for multi-scale analysis of physiological data and its serial changes over time is described and claimed in Shusterman granted U.S. patents and pending patent application referenced above. These patents and application are based on mathematical transformations and models, such as a linear orthogonal decomposition, and are presently the most accurate methods for compressing data and tracking changes in physiological data. Compressing the data and distributing processing among computing devices connected to a network (Internet cloud) minimizes the data-transmission time and tailors data processing to the computational resources of the network (including data-transfer rate and speed) and computing devices. The distributed processing is implemented by 1) constructing several information scales (levels or resolutions) that represent data and its most significant parameters at different levels of detail; and 2) exchanging the information between the scales. Low-resolution processing (Scale I) compresses the data into a small number of the most important primary elements, such as heart rate, blood pressure, oxygen saturation, respiration rate, and duration of electrocardiographic waves and intervals (PQ, QRS, and QT-intervals, amplitudes of P-, Q-, R-, S-, and T-waves). This low-resolution processing is implemented in a mobile device and works in real time. At intermediate-resolution processing (Scale II), the data and its serial changes are processed, compressed and analyzed, using a series of basis functions and their coefficients. At high-resolution processing (Scale III), serial changes in the physiological signals (data) and their combinations are processed, compressed and analyzed, using a mathematical transformation, such as a linear orthogonal transformation, to provide complete information about each signal and its dynamics. Thus, Scale I allows tracking most significant changes in real time using a portable, mobile, easy-to-use device. At the same time, the data is transmitted to a remote network/Internet server (cloud) for further processing at the higher resolution. The server for the higher-resolution analysis can be located in a medical center or another dedicated facility. The results of the high-resolution processing include:

personalized thresholds and alarms that are sent to the patient's mobile device, running PELEX HEART EXPERT PT software, for individual tailoring and fine-tuning of the real-time, low-resolution analysis and monitoring; and if necessary, compressed waveforms, numerical parameters (e.g., heart rate or blood pressure values, which can be color coded to facilitate review) and graphs/plots of data trends are transmitted in real time or with minimal delay to a cell phone (smart phone, mobile device) of a medical professional, running PELEX HEART EXPERT MD software, for display and review.

Figure 8:
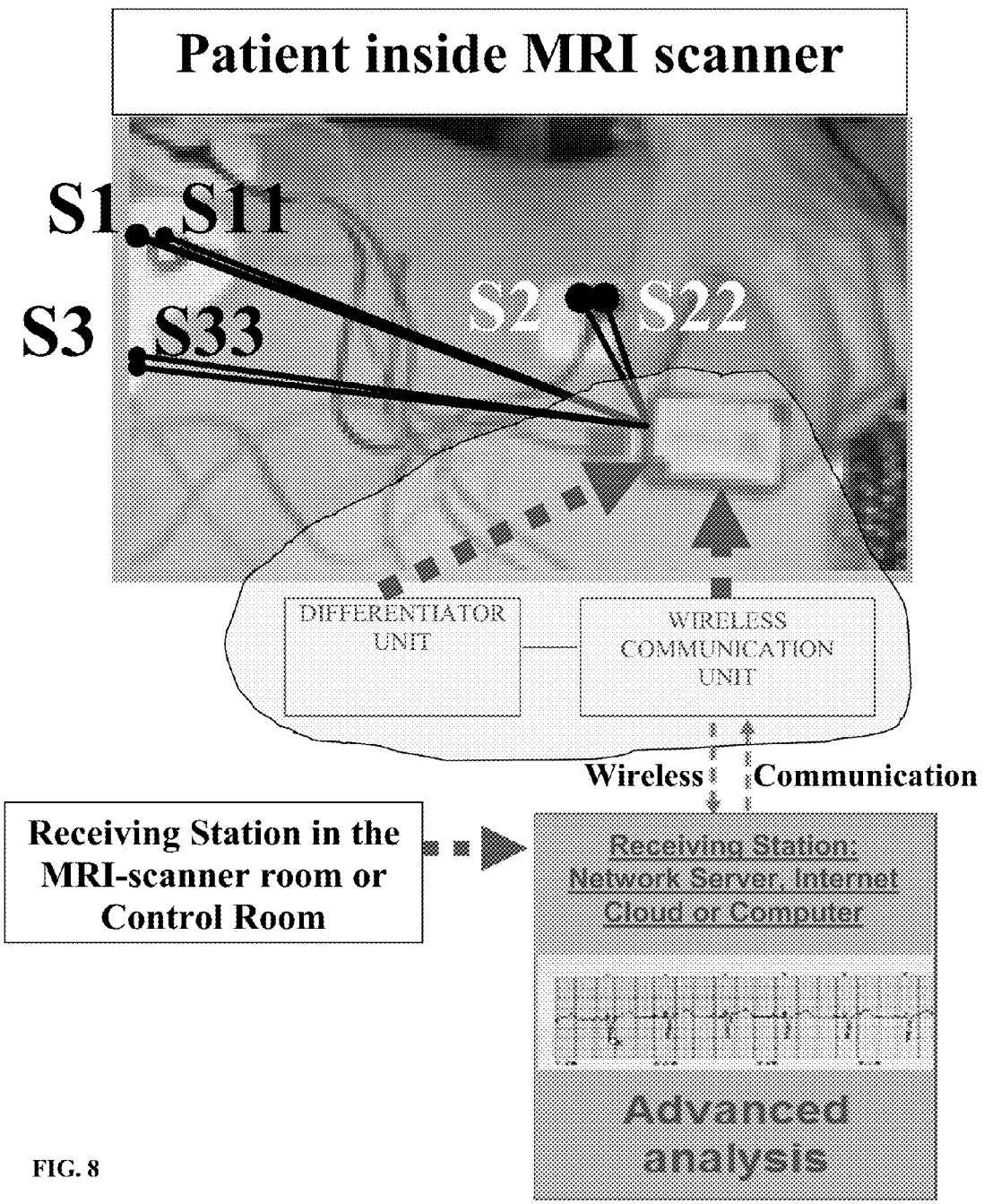
FIG. 8 is a block diagram of the implementation of present invention for magnetic-resonance imaging and filtering electromagnetic interference generated by the MR-scanner from physiological signals, such as an electrocardiogram, electroencephalogram, transthoracic resistance, blood pressure, respiration and oxygen saturation waveforms.

FIG. 8 shows the implementation of the multi-scale system for data processing and display in the MRI-environment. The signal Sig. 1 and the reference signal Ref. 1 are recorded from the same or close location by a single sensor (electrode) S1 or by separate sensors S1 and S11. Because of the same or similar location and simultaneous data collection, both sensors are subjected to the same electromagnetic interference (EMI). The signals collected by sensor S1 represent a sum of "true" physiological data, d1, and local EMI, n1, whereas data collected by sensor S11 represents local EMI only, n1. Therefore, subtracting the information collected by sensor S11 from that collected by sensor S1 provides filtered physiological data, FD1=d1+n1−n1=d1. This procedure can be repeated for all sensors, such as sensor S2 and reference sensor S22, sensor S3 and reference sensor S33 in FIG. 8 (e.g., all electrocardiographic leads) recorded at different locations, as well as for more complex types of EMI, which consist of several concurrent magnetic-field gradients, RF-pulses and other types of noise and/or interference. The subtraction can be implemented at the level of hardware, as a differential electronic cascade, as well at the level of firmware within the data acquisition unit or at the level of software. The operation can be adapted either by a user or by an algorithm, depending on the specific levels of EMI and data processing demands. In the latter scenario, the user reviews the data collected by sensors on a mobile device and/or on a computer station.

According to the data quality and the requirements of the data-processing application, the user turns the subtraction ON or OFF. If the subtraction is turned OFF, the signal from sensor S11 is collected along with other signals. This adaptive process can be also turned ON or OFF automatically by the software algorithm.

Figure 9:
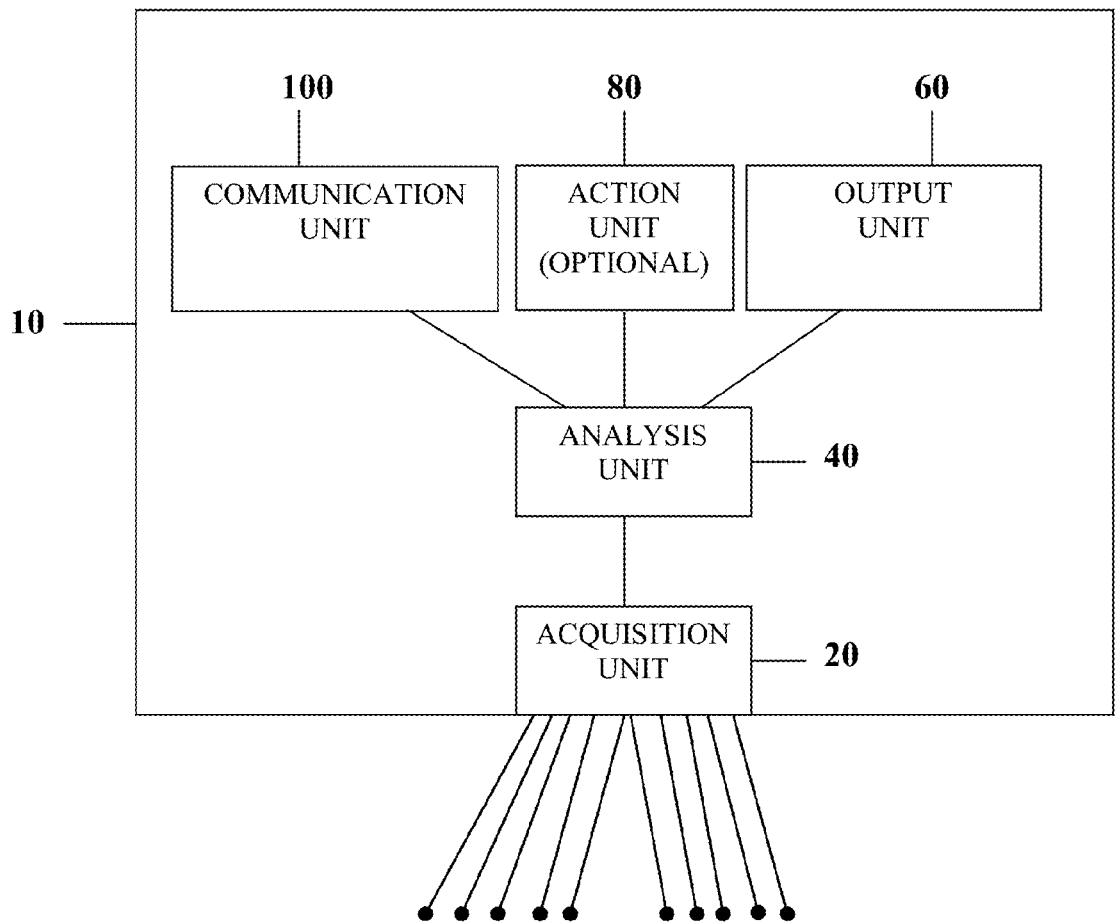
FIG. 9 is a block diagram of the multi-scale (multi-resolution, multi-level, multi-layer) method and system of the preferred embodiment of this invention.
Figure 10:
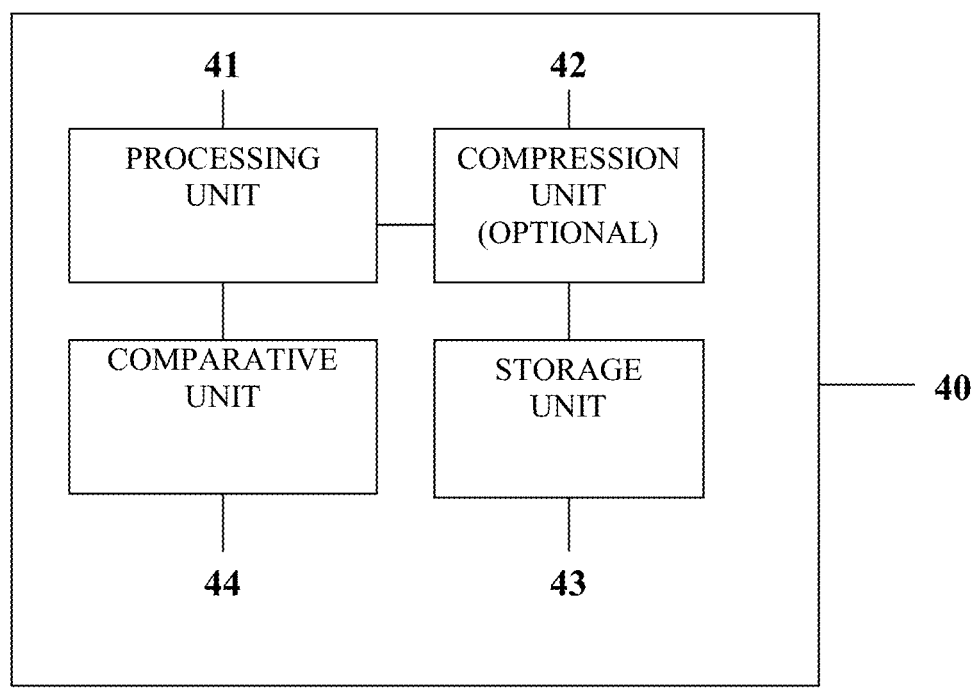
FIG. 10 is a block diagram of the analysis unit of a physiological monitoring system (for example, an electrocardiographic, ECG system), which is interfaced with the first level of the system of the present invention (to incorporate the ECG data, processed or unprocessed).

FIG. 9 is a block-diagram of a preferred embodiment of a system for at least one of information management, decision support, diagnosis, examination (physical, physiological, biochemical, etc.), monitoring, advice, medical recommendation, and bi-directional communication between individuals (patients), medical professionals (physicians, nurses, technicians) and medical centers. The system may receive physiological or health data (for example, ECG data) from a recorded data source for analysis, but preferably receives the data real-time, on-line. As used herein, patient means an animal, and most likely a human. The medical device further includes an analysis unit or module 40 which, in turn, consists of processing, compression, storage, and comparison units (FIG. 10). The processing unit 41 can be a typical computer or personal computer of the type available from many vendors such as IBM or Hewlett-Packard. The processing unit 41 is programmed to detect a plurality of characteristic points such as the onset, peak and offset of P-, Q-, R-, S-, T-, U-waves, and computes the characteristic parameters or primary elements which include amplitudes of the said waves and ST-segment, duration of PQ-, QRS-, and QT-intervals. The processing unit 41 has a programmable microprocessor that can be programmed to modify or change the set of primary elements or to adjust their search criteria. This allows individual adjustment of the characteristic points which, in turn, increases the accuracy of detection of the primary elements. For instance, in signals with biphasic T-wave, two T-peaks should be detected, whereas monophasic T-wave requires detection of a single T-peak. Furthermore, the criteria for determining the offset of biphasic T-wave are different from the criteria for the offset of monophasic T-wave. Individual adjustment of the primary elements and their search criteria increases the accuracy of the detection of characteristic points in different ECG patterns. Still another possibility is analysis of combined changes in some primary elements or disabling analysis of the other elements. For example, in patients with possible electrolyte abnormalities, the amplitudes of the T-wave and U-wave may be combined into a single index which will be convenient for monitoring. Furthermore, the set of monitored primary elements can be modified according to the specifics of cardiovascular abnormality. For example, in patients with coronary artery disease, the amplitude and the slope of the ST-segment should be monitored continuously. However, its initial or chronic displacement (e.g., chronic ST-depression) might require an individual threshold adjustment to improve separation of chronic from acute changes.

Figure 11:
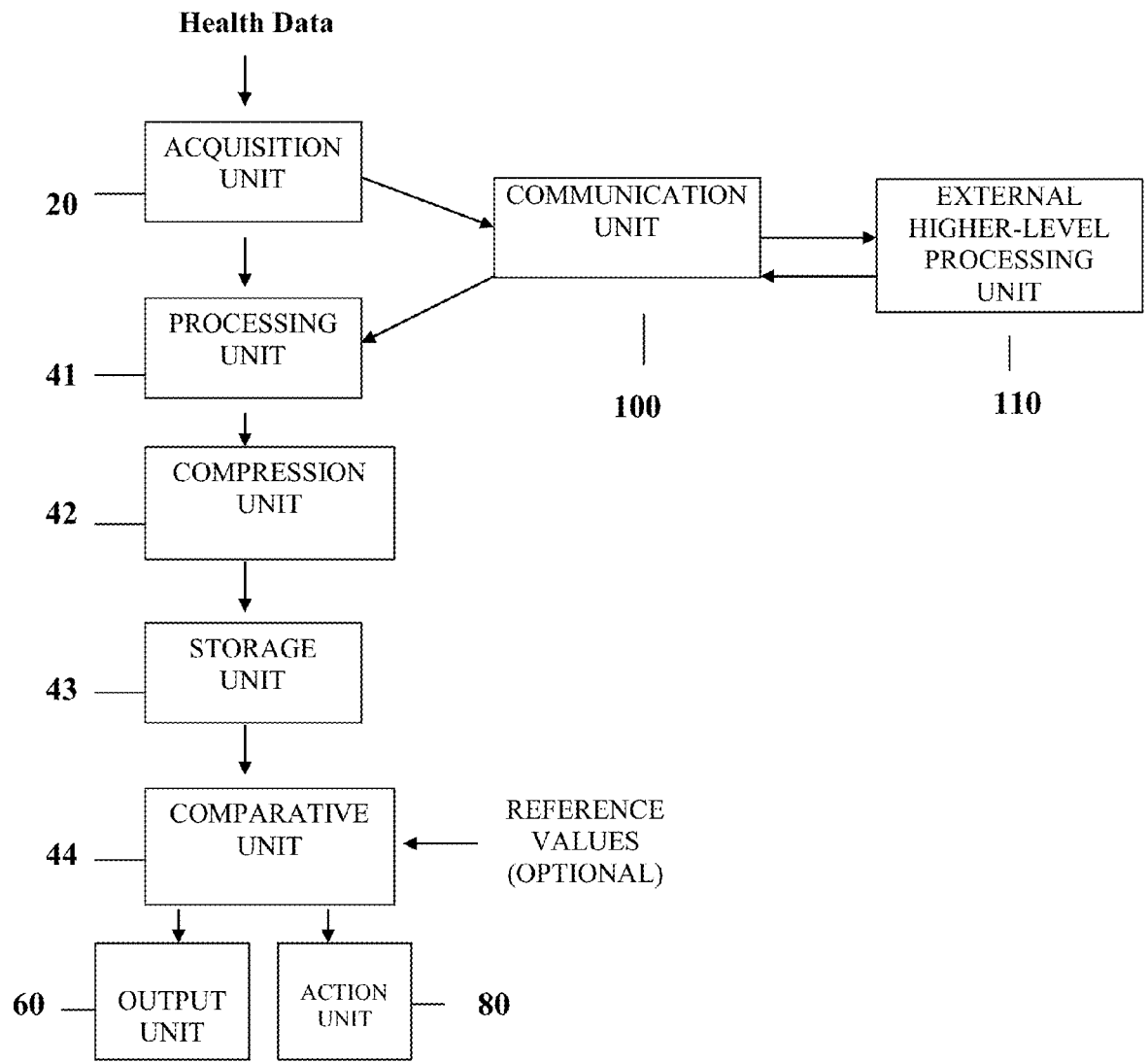
FIG. 11 is a flowchart of operation of the preferred embodiment.

FIG. 11 is a flowchart of the operation of the preferred embodiment. Compression unit 42 compresses the ECG waveform into a few weighted basis vectors and their coefficients using principal component analysis, wavelet decomposition, or other orthogonal mathematical transformation. Storage unit 43 stores the compressed waveforms and the computed primary elements into memory. Comparative unit 44 compares the newly acquired waveforms and newly computed primary elements with the waveforms and primary elements previously stored in the storage unit 43. The analysis unit 40 has means for adjusting the thresholds for each indicator, whereas the default values correspond to normal ECG. An output unit 60 includes a screen or a set of indicators for displaying the ECG waveforms and the computed primary elements in comparison with the previously stored primary elements or in comparison with the default reference values. The results of comparison can be represented both qualitatively and quantitatively in the dynamic and static modes. Abnormal readings may be further classified into moderately abnormal and severely abnormal. To make the indicators understandable to a lay person, the degree of abnormality may be color-coded: green color corresponds to a normal value, yellow corresponds to a moderate abnormality, and red corresponds to a severe abnormality. In the dynamic mode, the quantitative representation shows the differences between the newly acquired and stored primary elements and waveforms, whereas the qualitative representation includes indication of each parameter as being changed (C) or unchanged (U). The output unit 60 may alternatively or additionally feed an output data to an action unit 80 for sounding an alarm, generating a vibration, or taking appropriate measures, such as applying the drugs or adjusting the therapy mode. Communication unit 100 transmits the information between the device 10 and external higher-level processing device 110. The communication unit 100 may be a modem or a wireless transmitter/receiver. Electrocardiographic signals and recorded values of primary elements and indexes are transmitted from the device 10 to higher level devices for more detailed processing and storage. The higher-level device 110 preferably transmits back to device 10 a set of primary elements and their search criteria to be used in device 10.

EXAMPLE 1

Application for Remote Management of Patients with Heart Failure

Congestive heart failure (CHF) afflicts more than 5 million Americans, causing over a million hospital admissions every year. The estimated annual cost of this illness to the US economy is $39 billion. One half of these costs can be attributed to hospitalizations related to CHF decompensation, and nearly half of hospital readmissions are caused by medication or dietary nonadherence. Assessing CHF progression is challenging, because the standard-of-care periodic evaluations of body weight, blood pressure, and clinical symptoms cannot provide an early indication of CHF worsening. Moreover, recently introduced implantable sensors for tracking intrathoracic fluid accumulation (which are costly, require time-consuming insertion procedures, and carry the risk of complications) have not produced consistent results.

For remote monitoring of CHF patients at home, they are given:
  miniaturized data collection modules (DCM) shown in FIG. 4.;
  off-the-shelf ECG electrodes;
  instructions for attaching the electrodes and operating the monitors.

The DCM are attached to the ECG electrodes and activated by the patients 5 minutes before the start of the 6-minute walk; they are turned off and disconnected 10 minutes after the exercise. The data are recorded onto a flash memory card located inside the DCM. In addition, the patients receive daily automatic text reminders (30 minutes before the start of the 6-minute walk) via the cell-phone communication link. The 12-lead, high-fidelity ECG, physical activity, changes in body position, as well as clinical dynamics (shortness of breath, chest pain) are recorded by patients daily during the 6-minute walk and sent via the cell-phone communication link to the cloud for processing. Physicians are able to track the dynamics of patients' waveforms (ECG, blood pressure, respiration rate, oxygen saturation, as well as their speed during exercises) from their smart phones, which receive these data from the cloud in a compressed form. Cardiologists and exercise physiologists can track the dynamics of ECG, blood pressure and respiration during exercise in real time on the display of their smart phones connected to the cloud. If the ECG starts showing potentially life-threatening abnormalities (signs of cardiac ischemia) or significant changes in blood pressure or respiration rate, the physicians can stop the exercise. Alternatively, the cloud system can monitor changes in these parameters using its automatic processing software algorithms with personalized thresholds and alarms (which are adjusted according to the individual reference values, as described above). If the changes in the vital signs exceed these personalized thresholds, the cloud sends an alarm and compressed data to the physician's smart phone for review; and at the same, it sends a message to the patient to stop exercising (walking). The personalized thresholds are determined automatically by the cloud software (e.g., personalized range of normal heart rate, blood pressure, respiration rate, etc.). Alternatively, these thresholds can be manually changed in the cloud's database by medical professionals, using their smart phones for communicating with the cloud; after that, updated thresholds are sent to the patient's smart phone to update/replace previous threshold settings in the smart phone's software automatically.

If the software and/or attending physicians (reviewing the compressed data downloaded from the server to their smart phones in real time) detect life-threatening changes, an immediate change in patient's management can be initiated. If the changes in patient status are life threatening, the cloud software and/or physicians from their smart phones send an alarm to dispatch an ambulance and to alert the Emergency Medical Services (EMS) personnel.

EXAMPLE 2

Application for Remote Detection and Differential Diagnosis of Syncope

Syncope (loss of consciousness) accounts for 3-5% of emergency department visits and 1-6% of all urgent hospital admissions in the US. As many as 1-2 million Americans are evaluated annually for syncope, and the costs associated with diagnostic tests, hospitalization and clinical management are overwhelming. The diagnostic evaluation is complicated by an extensive range of possible etiologies, from cardiac to neurological and psychiatric disorders. Furthermore, up to 47% of patients may be discharged without final diagnosis, and the 1-year mortality rate in syncope of cardiac origin could reach 18-33%. This indicates the need and importance of developing clinical diagnostic modalities that could help differentiate between benign and life-threatening etiologies of syncope.

By allowing simultaneous collection of a high-quality (diagnostic) 12-lead ECG, physical activity and body position over prolonged periods of time, the PELEX system with distributed processing can eliminate the need for multiple, sequential diagnostic ECG tests, which include Holter, event and ambulatory telemetry ECG monitoring. This will shorten the time from initial evaluation to final diagnosis and reduce associated costs.

The DCM is given to patients for continuous monitoring of 12-lead ECG, blood pressure, physical activity and body position. The data is collected continuously over a 30-day period, compressed and either stored on a local memory card or transmitted in a real-time to the cloud for further processing. The episode of syncope is manifested by a sudden fall (detected by the 3-axial accelerometer sensor.) Simultaneous measurements of physical activity (the impact of previous activity level), electrocardiogram (for diagnosing arrhythmia), blood pressure (for detecting sudden pressure drop) help in identifying the mechanism of syncope. The data may also include blood pressure measured from several sensor locations, pulse transit time, pressure wave, its amplitude and duration. The data are compressed by the smart phone app and sent to the cloud for further processing, compression and conditioning. From the cloud, processed and compressed signals (ECG, blood pressure, physical activity and body position) are sent to the physician's smart phone for display and review. The analysis on the cloud can identify periods of sudden changes in body position (fainting) and send only those periods to the physician's smart phone for review. The criteria and time intervals for sending such data can be adapted to the specifics of the patient's medical status and physician's preferences. This adaptation can be achieved using physiological basis functions disclosed in Shusterman patent application Ser. No. 12/885,520, filed on Sep. 19, 2010.

Whereas particular aspects of the method of the present invention and particular embodiments of the invention have been described for purposes of illustration, it will be appreciated by those skilled in the art that numerous variations of the details may be made without departing from the invention as described in the appended claims.

What is claimed is:

1. A method for adaptive, multi-level processing of health data with said processing levels distributed among computing devices connected to a network of computers, said method comprising:
    collecting at least one signal of an individual's health data by substantially continuous monitoring said health data;
    sending said at least one signal to a first computing device for first-level processing which includes detecting a plurality of primary elements of said data and processing said primary elements in low resolution to generate data respecting time intervals or amplitudes of said primary elements, storing reference values of said primary elements, and comparing said reference values with newly received data to produce qualitative indicators and quantitative data of differences between said reference values and said newly received data;
    sending said signal after said first-level processing to a second computing device for second-level processing at higher resolution and analysis of changes, selected from at least one of continuous and serial changes, in at least some of the said primary elements in said data, using at least one method selected from mathematical decomposition and methods of artificial intelligence to improve at least one of said first-level and second-level processing, said second-level processing being adapted to correspond to at least one parameter selected from the user commands and computational resources of the network and said first and second computing devices;
    exchanging information between said first-level and second-level processing, said exchanging adapted to correspond to at least one parameter selected from the network data-transfer rate, user commands and computational resources of said first and second computing devices; and
    displaying at least the results of one of said first-level and second-level processing.

2. A method as set forth in claim 1 in which said computing devices are connected to at least one of a network of computers and the Internet.

3. A method as set forth in claim 1 that includes exchanging information between said two levels of processing to adapt and coordinate said two levels of processing with respect to at least one feature selected from speed, accuracy and display of said signal.

4. A method as set forth in claim 1 in which said signal that is compressed is stored in said remote computing device.

5. A method as set forth in claim 1 in which results of the second-level processing are displayed both quantitatively and qualitatively.

6. A method as set forth in claim 1 in which said at least one signal is collected from an MRI scanner.

7. A method as set forth in claim 6 in which at least a reference signal and a physiological signal are collected from substantially the same location on a subject and the reference signal is subtracted from the physiological signal to improve accuracy of the analysis.

8. A system for adaptive, multi-level processing of health data with said processing levels distributed among computing devices connected to a network of computers, said system comprising;
    at least one sensor for collecting at least one signal of an individual's health data by substantially continuous monitoring said health data;
    at least one mobile (first) computing device for receiving said at least one signal and performing first-level processing of said at least one signal which includes detecting a plurality of primary elements of said data and processing said primary elements in low resolution to generate data respecting time intervals or amplitudes of said primary elements, storing reference values of said primary elements, and comparing said reference values with newly received data to produce qualitative indicators and quantitative data of differences between said reference values and said newly received data;
    said at least one mobile computing device further having communication capability and software for network communication with at least one second computing device, which is adapted to perform second-level (higher-resolution) processing and analysis of changes, selected from at least one of continuous and serial changes, in at least some of the said primary elements in said data, using at least one method selected from mathematical decomposition and methods of artificial intelligence to improve at least one of said first-level and second-level processing, said second-level processing adapted to correspond to at least one parameter selected from the user commands, computational resources of a network and said first and second computing devices, and said mobile computing device further having communication capability for exchanging information with said second computing device to coordinate said two levels of processing using at least one parameter selected from the network data-transfer rate, user commands and computational resources of said first and second computing devices; and
    said at least one mobile computing device having a display unit for presentation of said at least one signal and primary element, said presentation adapted to correspond to computational resources of said network, first computing device and second computing device.

9. A system as set forth in claim 8 in which said computing devices are connected through the Internet network.

10. A system as set forth in claim 8 in which said second computing device to perform second-level processing is selected from a network server and the Internet server.

11. A system as set forth in claim 8 in which said at least one mobile computing device is a cell phone.

12. A system as set forth in claim 8 in which said at least one signal is collected from an MRI scanner.

13. A system as set forth in claim 8 which includes a storage unit for storing the compressed signal to buffer said exchanging of information between computing devices.

14. A system as set forth in claim 8 which includes a compression unit that compresses waveforms using at least one type of mathematical transformation.

\* \* \* \* \*